US011413320B2

(12) United States Patent
Powell et al.

(10) Patent No.: US 11,413,320 B2
(45) Date of Patent: Aug. 16, 2022

(54) ANTIVIRAL COMPOSITIONS AND METHODS

(71) Applicant: MOREHOUSE SCHOOL OF MEDICINE, Atlanta, GA (US)

(72) Inventors: Michael D. Powell, Douglasville, GA (US); Erick Vidjin' Agnih Gbodossou, Dakar-Etoile (SN)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 215 days.

(21) Appl. No.: 16/718,994

(22) Filed: Dec. 18, 2019

(65) Prior Publication Data

US 2020/0197469 A1 Jun. 25, 2020

Related U.S. Application Data

(60) Provisional application No. 62/783,035, filed on Dec. 20, 2018.

(51) Int. Cl.
*A61K 36/42* (2006.01)
*A61K 9/14* (2006.01)
*A61P 31/18* (2006.01)
*A61K 9/20* (2006.01)
*A61K 38/10* (2006.01)
*A61K 9/48* (2006.01)

(52) U.S. Cl.
CPC ............... *A61K 36/42* (2013.01); *A61K 9/14* (2013.01); *A61K 9/20* (2013.01); *A61K 9/48* (2013.01); *A61K 38/10* (2013.01); *A61P 31/18* (2018.01)

(58) Field of Classification Search
CPC ............................... A61P 31/18; A61K 36/42
See application file for complete search history.

(56) References Cited

U.S. PATENT DOCUMENTS

| 2002/0182272 A1 | 12/2002 | Halstead |
| 2011/0229604 A1 | 9/2011 | Real |
| 2012/0009286 A1 | 1/2012 | Gbodossou |

FOREIGN PATENT DOCUMENTS

| KR | 20130129159 A | * 11/2013 |
| WO | 02/062364 | 8/2002 |
| WO | 2016181214 | 11/2016 |

OTHER PUBLICATIONS

Yao (Immunoaffinity purification of alpha-momorharin from bitter melon seeds (*Momordica charantia*, J. Sep. Sci. 2011,34, 3092-3098) (Year: 2011).*
KR-20130129159-A translated doc (Year: 2013).*
International Search Report and Written Opinion of International Application No. PCT/US19/67165 dated Apr. 2, 2020.
UniProt AOA1S3AVV6. Acidic endochitinase-like, Sep. 27, 2017 [online]. [Retrieved Mar. 11, 2020], Retrieved from the internet: <URL: https://www.uniprot.org/uniprot/AOA1S3AW6.txt?version=5>. Especially p. 1.
Uniprot AOAOAOL62. Uncharacterized protein, Nov. 7, 2018 [online]. [Retrieved Mar. 11, 2020). Retrieved from the internet: <URL: https://www uniprot org/uniprot/AOAOAOI621.txt?version=14> Especially p. 1.
International Preliminary Report on Patentability of International Application No. PCT/US2019/067165 dated Jul. 1, 2021.
Gbodossou, E. V. A., The Efficacy of African Herbal Medicine (METRAFAIDS) in the Treatment of HIV Positive African Populations—Report of Clinical Observational Study, Prometra (Association for the Promotion of Traditional Medicine).
Vasisht, K. et al., "Compedium of Medicinal and Aromatic Plants", ICS Unido 2004, pp. 1-124.
Indigenous African Plant-Based Extracts provide promising preliminary results against Ebola Virus, www.msm.edu/RSSFeedArticles/AfricasAnswertoEbola.php, pp. 1-4.
Senegal: Traditional Medicine Treatment for Aids Passes Clinical Tests, allAfrica.com.
Amzat, J. et al., "Roles of Traditional Healers in the Fight Against HIV/AIDS", Ethno-Med., 2008, vol. 2(2), pp. 153-159.
Sun, Y. et al., "Mono-PEGylation of Alpha-MMC and MAP30 from Momordica charantia L.: Production, Identification and Anti-Tumor Activity", Molecules, 2016, vol. 21(11), pp. 1-9.
Kesari, P. et al., "Structural and functional evolution of chitinase-like proteins from plants", Proteomics, 2015, vol. 15, pp. 1693-1705.
Fan, X. et al., "A-MMC and MAP30, two ribosome-inactivating proteins extracted from Momordica charantia, induce cell cycle arrest and apoptosis in A549 human lung carcinoma cells", Mol. Med. Rep., 2015, vol. 11(5), pp. 3553-3558.
Schrot, J. et al., "Ribosome-inactivating and related proteins", Toxins, 2015, vol. 7(5), pp. 1556-1615.

* cited by examiner

*Primary Examiner* — Terry A McKelvey
*Assistant Examiner* — Jacob A Boeckelman
(74) *Attorney, Agent, or Firm* — Ping Wang; Rimon Law

(57) ABSTRACT

The present application relates to a compositions and methods comprising or expressing a MOMO30 protein derived from *Momordica balsamina*. The MOMO30 protein is about 30 kDa in size, is stable after being autoclaved at 120° C. for 30 min, resists proteolytic cleavage by trypsin, exhibits mannose-sensitive binding HIV gp120, exhibits hemagglutinin and chitinase activity, is capable of activating and stimulating T cell proliferation, is capable of preventing infection by HIV-1 or alleviating symptoms in an HIV-1 infected patients and comprises the amino acid sequence of SEQ ID NO: 1. The MOMO30 protein and/or a nucleic acid encoding the same may be used in methods for preventing or treating viral infections by HIV and other enveloped viruses.

6 Claims, 22 Drawing Sheets

Specification includes a Sequence Listing.

| Extracts | Hela | | | HFF | | |
|---|---|---|---|---|---|---|
| | EC50, µg/ml | SD | SI | EC50, µg/ml | SD | SI |
| MSM A | 81.94 | 18.73 | 3 | 5.21 | 1.86 | >192 |
| MSM A-rep2 | 93.02 | 20.29 | 3 | 45.25 | 10.16 | >22 |
| MSM B | 14.49 | 3.59 | 69 | 242.53 | 40.61 | >4 |
| MSM B-rep2 | 15.37 | 4.46 | 65 | 285.42 | 34.12 | >4 |
| MSM C | 119.95 | 21.27 | 8 | 207.78 | 29.73 | >5 |
| MSM C-rep2 | 132.63 | 19.08 | 8 | 428.47 | 48.28 | >2 |
| MSM D | 10.42 | 2.27 | 96 | 222.37 | 36.77 | >4 |
| MSM D-rep 2 | 11.96 | 2.43 | 84 | 245.02 | 37.5 | >4 |
| MSM E | 76.49 | 15.16 | 13 | 40.97 | 10.35 | >24 |
| MSM E-rep2 | 87.22 | 41.51 | 11 | 181.73 | 53.39 | >6 |
| MSM A-E | 32.93 | 9.59 | 30 | 97.29 | 135.7 | >10 |
| MSM A-E-rep2 | 38.4 | 17.44 | 26 | 163.12 | 35.44 | >6 |

```
┌─────────────────────────────────────┐
│   Dried plants extracted in water   │
└─────────────────────────────────────┘
                 ⇩
┌─────────────────────────────────────┐
│          Plant cells lysed          │
└─────────────────────────────────────┘
                 ⇩
┌─────────────────────────────────────┐
│  Plant cell lysate centrifuged to   │
│   remove debris and particulates    │
└─────────────────────────────────────┘
                 ⇩
┌─────────────────────────────────────┐
│ Clarified plant cell lysates run    │
│ through MW cut-off filter to        │
│ sterilize and further purify MOMO30 │
│ protein in retentate                │
└─────────────────────────────────────┘
                 ⇩
┌─────────────────────────────────────┐
│ MOMO3-containing retentate          │
│ resuspended in buffer for further   │
│ analysis, immunoaffinity            │
│ purification and/or storage         │
└─────────────────────────────────────┘
```

FIG. 7

| Patient | | CD4 | | | Viral Load | |
|---|---|---|---|---|---|---|
| | Baseline | 6-Month | 180-Month | Baseline | 6-Month | 180-Month |
| PROM050 | 254 | 593 | 112 | 21450 | 12144 | <20 |
| PROM052 | 137 | 472 | 283 | 65400 | 34880 | <20 |
| PROM074 | 472 | 787 | 61 | 400 | 280 | <20 |
| PROM062 | 273 | 783 | 78 | 81700 | 3000 | <20 |
| PROM070 | 378 | 922 | 73 | 92257 | 2325 | <20 |
| PROM057 | 218 | 498 | 314 | 126220 | 178860 | <20 |
| PROM055 | 582 | 957 | 649 | 17353 | 8142 | <20 |
| PROM067 | 406 | 518 | 180 | 210025 | 89160 | <20 |
| PROM072 | 231 | 377 | 146 | 546256 | 5025 | 3360 |
| PROM064 | 445 | 1216 | 95 | 23757 | 623 | 3600 |
| PROM060 | 178 | 488 | 110 | 724 | 21283 | <20 |
| PROM059 | 179 | 615 | 969 | 83125 | 67250 | 20 |
| PROM066 | 600 | 837 | 95 | 178180 | 400 | <20 |

FIG. 15C

FIG. 16A
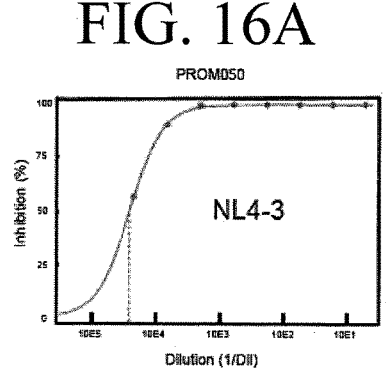
PROM050 NL4-3
FIG. 16B
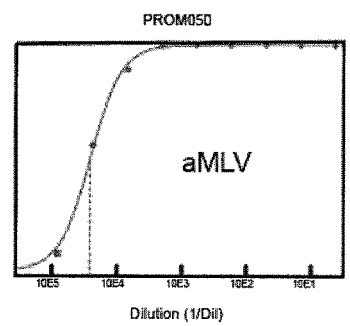
PROM050 aMLV
FIG. 16C
| Patients | VL | Primary Isolates | | | | | | | | | | Lab strains | | |
|---|---|---|---|---|---|---|---|---|---|---|---|---|---|---|
| | | 94UG103 | 92BR020 | 93IN905 | MGRM-C-026 | 92TH021 | MGRM-AG-007.c14 | MGRM-AG-008.c16 | MGRM-AG-009.c10 | MGRM-AG-011.c01 | CAP210-2-00-E8 | JRCSF | NL43 | aMLV |
| PROM050 | ND | 20,779 | 23,339 | 23,593 | 25,635 | 20,325 | 23,491 | 23,439 | 24,658 | 27,203 | 23,758 | 24,144 | 25,220 | 23,545 |
| PROM052 | ND | 29,781 | 31,849 | 30,054 | 27,099 | 31,220 | 29,192 | 31,710 | 30,741 | 44,497 | 31,582 | 34,644 | 31,308 | 25,646 |
| PROM074 | ND | 5,453 | 5,230 | 5,127 | 5,033 | 4,283 | 5,202 | 5,570 | 4,833 | 8,027 | 5,509 | 5,542 | 4,924 | 4,559 |
| PROM062 | ND | 5,039 | 5,365 | 4,929 | 5,048 | 4,827 | 5,101 | 5,718 | 5,787 | 6,795 | 5,420 | 4,287 | 5,311 | 4,506 |
| PROM070 | ND | 4,088 | 4,971 | 4,808 | 5,043 | 4,844 | 4,579 | 4,827 | 4,745 | 5,558 | 5,046 | 4,418 | 4,272 | 5,008 |
| PROM057 | ND | 2,984 | 3,755 | 3,802 | 3,696 | 4,364 | 4,076 | 4,000 | 4,161 | 4,452 | 3,870 | 3,310 | 4,088 | 3,802 |
| PROM055 | ND | 561 | 610 | 690 | 771 | 576 | 572 | 599 | 581 | 643 | 716 | 667 | 620 | 563 |
| PROM067 | ND | 27 | 21 | 28 | 21 | 19 | 19 | <10 | <10 | 19 | 14 | 12 | 1,120 | 15 |
| PROM072 | 3360 | 63 | 96 | 389 | 288 | 53 | 34 | 18 | 15 | 20 | 49 | 69 | 739 | 22 |
| PROM064 | 3600 | 60 | 239 | 199 | 26 | 64 | 82 | 52 | 14 | 50 | 53 | 26 | 672 | 22 |
| PROM060 | ND | 17 | 11 | <10 | <10 | <10 | <10 | <10 | <10 | <10 | <10 | <10 | 433 | <10 |
| PROM059 | 20 | 41 | 122 | 47 | 61 | 23 | 23 | 20 | 16 | 29 | 64 | 34 | 111 | 25 |
| PROM066 | ND | <10 | <10 | <10 | <10 | <10 | 12 | <10 | <10 | <10 | <10 | <10 | 93 | 10 |
| Controls | | | | | | | | | | | | | | |
| PROM053 (-) | ND | <10 | 19 | <10 | <10 | <10 | <10 | <10 | <10 | <10 | <10 | <10 | <10 | 18 |
| PROM054 (-) | ND | 43 | 30 | 17 | 30 | 25 | 29 | 18 | 26 | 12 | 25 | 11 | 28 | 35 |
| PROM058 (-) | ND | 40 | 38 | 30 | 53 | 47 | 48 | 33 | 29 | 30 | 29 | 37 | 30 | 35 |
| Z23 (+) | | 195 | 452 | 330 | 400 | 297 | 193 | 167 | 134 | 855 | 193 | 379 | 2,912 | <100 |
| Z23 (+) | | 208 | 616 | 259 | 432 | 271 | 160 | 148 | 120 | 861 | 172 | 339 | 2,736 | <100 |
| Z23 (+) | | 205 | 712 | 283 | 234 | 312 | 171 | 146 | 133 | 856 | 195 | 297 | 2,797 | <100 |

FIG. 18A

GPIVTYWGQNVXEGEL (SEQ ID NO: 1)

FIG. 18B

```
                       Signal peptide
                                    GPIVTYWGQNVXEGEL
XP_028786671.1  MSSKTQALVLLLSPLLLLSHLSSSQGCPIVTYWGQNVNEGELSTACDTRKYEIINIAFMNTFGNGQTPNIDLSGHCSESW  80
XP_028786682.1  MASKTQAFVLLLWPLLLLSHLSSSQSCPIVTYWGQNVNEGELDAACLTKRYEIINIAFMNTFGNGQTPDINLSGHCSESW  80
XP_028773277.1  MSYKTQALVLLLSPLLLLSHLSSSQGCPIVTYWGQNVNEGELSTACDTGKYEIINIAFMNTFGNGQTPNIDLSGHCSESW  80
XP_028773263.1  MSSKTQALVLLLSPLLLLSHLSSSQGYPIVTYWGQNVNEGELSTACDTGKYEIINIAFMNTFGNGQTPNIDLSGHCSESW  80
XP_028773269.1  MSSKTQALVLLLSPLLLLSHLSSSQGCPIVTYWGQNVNEGELSTACDTGKYEIINIAFMNTFGNGQTPDINLAGHCSASW  80
XP_028786677.1  MASKTQALVLLLWPLMLLSHLSSSQSCPIVTYWGQNVNEGELDAACQTEKYEIINIAFMNTFGNGQTPDINLAGHCHWSW  80
XP_028773281.1  MSSKTQALVLLLSPLLLLSHLSSSQGCPIVTYWGQNVNEGELST-----------------FGNGQTPDINLAGHCYASW  63
XP_028773268.1  MASKTQALVLLLWPLLLLSHLSSSQSCPIVTYWGQNVNEGELDAACQTKKYEIINIAFMNTFGNGQTPDINLAGHCSASW  80
XP_028773271.1  MASKTQALVLLLWPLLLLSHLSSSQSCPIVTYWGQNVNEGELDAACQTKKYEIINIAFMNTFGNGQTPDINLAGHCHWSS  80
XP_028788031.1  MASKPQALVLLLWPLLLLSHLSSSLSCPIVTYWGKNVNEGELDAACQTKKYEIINIAFMNTFGNGQTPDINLAGHCHWSW  80
```

FIG. 18C

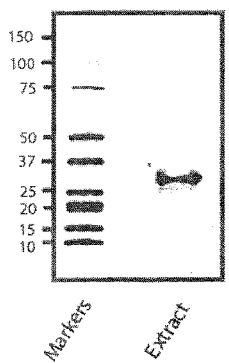

FIG. 18D

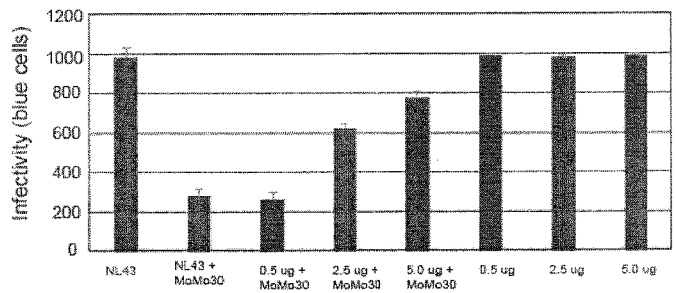

ated antiretroviral resistance. Most importantly, treatment must be maintained for the life of the patient in ordered to maintain the benefits. In the vast majority of cases, withdrawal of HAART results in rebound of viral loads and disease progression. HAART is expensive to maintain and is beyond the means of many individuals in third-world countries. This is particularly true in African populations, which have the highest incidence of HIV/AIDS.

ANTIVIRAL COMPOSITIONS AND METHODS

This application claims the benefit of U.S. Provisional Application Ser. No. 62/783,035, filed Dec. 20, 2018. The entirety of the aforementioned application is incorporated herein by reference.

FIELD

The present application generally relates to antiviral compositions and methods. More particularly, the present application relates to antiviral compositions comprising a plant MOMO30 protein for treatment and prevention of viral inventions.

BACKGROUND

The conventional approach to HIV treatment, highly active anti-retroviral therapy (HAART) involves the use of combinations of anti-retrovirals such as bictegravir/tenofovir alafenamide/emtricitabine (Biktarvy), dolutegravir (Tivicay) plus tenofovir/emtricitabine (Truvada), raltegravir (Isentress) plus tenofovir/emtricitabine (Truvada), and abacavir/dolutegravir/lamivudine (Triumeq). HAART enables the reduction of blood plasma viral load to undetectable levels for extended periods of time. On average, 50% of patients see their plasma viral loads fall to less than 50 copies/ml after a treatment of around 12 months. However, antiviral treatments, including HAART are not without flaws and do not carry the assurance of a long-term cure.

Suppression of viral loads and slowing of the reduction in in CD4 counts allows for prolonged periods of relatively normal life. However, even newer formulations of HAART have associated toxicity and risk of developing antiretroviral resistance. Most importantly, treatment must be maintained for the life of the patient in ordered to maintain the benefits. In the vast majority of cases, withdrawal of HAART results in rebound of viral loads and disease progression. HAART is expensive to maintain and is beyond the means of many individuals in third-world countries. This is particularly true in African populations, which have the highest incidence of HIV/AIDS.

In view of the foregoing, there is a need for improved and less costly therapeutic options for treating HIV and other viral infections. In particular, there is a need for a treatment that can be administered short-term and induce a long suppression of viral loads.

SUMMARY

In one aspect, the present application relates to a composition comprising or expressing a MOMO30 protein. The MOMO30 protein has a size of about 30 kDa, is capable of binding HIV gp120, is stable to both heat and protease treatment, is non-toxic to cells at therapeutic levels, and can block the interaction of viral glycoproteins to cellular receptors resulting in inactivation of an enveloped virus, such as HIV-1.

In another aspect, the present application relates to a method for preventing or reducing symptoms of HIV infection, comprising orally administering to a subject in need thereof an effective amount of a MOMO30 protein composition prepared by a method includes the steps of: (a) drying plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; and (e) forming the MOMO30 protein composition by: (i) passing the clarified plant cell lysate through a molecular weight cut-off filter and collecting the MOMO30-containing retentate; or (ii) purifying the MOMO30 protein from the clarified plant cell lysate by immunoaffinity purification using an anti-MOMO30 antibody. The MOMO30 protein composition formed therefrom is orally administered to the subject in liquid or dried form such that the MOMO30 protein composition is substantially free of plant components less than 10 kDa in size and includes a protein of about 30 kDa in size that is stable after boiling at 100° C. for 20 min, that binds HIV gp120, and comprises the amino acid sequence of SEQ ID NO: 1.

In certain preferred embodiments, the plant comprising MOMO30 protein is a member of the *Momordica* genus. In a more particular embodiment, the plant is *Momordica balsamina*.

In some embodiments, the method for preparing the MOMO30 protein composition comprises the step of subjecting the plant extract to immunoaffinity purification prior to administration. In other embodiments, the method includes the step of eluting the MOMO30 retentate in an aqueous buffer to form an aqueous MOMO30 protein composition in solution.

In some embodiments, the MOMO30 protein composition is dried and administered to the subject in a dried form. In some embodiments, the MOMO30 protein composition is dried and orally administered to the subject in a dried form, such as a capsule or tablet. In other embodiments, the MOMO30 protein composition is administered to the subject in liquid form. In certain particular embodiments the MOMO30 protein composition is formulated as an herbal tea for oral administration in liquid form.

In another aspect, a method for preparing a MOMO30 protein composition, includes the steps of: (a) drying a plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; and (e1) passing the plant cell lysate through a molecular weight cut-off filter and collecting the MOMO30-containing retentate, or (e2) purifying the MOMO30 protein from the clarified plant cell lysate by immunoaffinity purification using an anti-MOMO30 antibody, such that the MOMO30 protein composition formed therefrom is substantially free of plant components less than 10 kDa in size and includes a protein of about 30 kDa in size that is stable after boiling at 100° C. for 20 min, that binds HIV gp120, and that comprises the amino acid sequence of SEQ ID NO: 1.

In certain preferred embodiments, the plant comprising MOMO30 protein is a member of the *Momordica* genus. In a more particular embodiment, the plant is *Momordica balsamina*.

In another aspect, the present application provides a pharmaceutical composition containing MOMO30 protein for preventing or reducing symptoms of HIV infection in which the pharmaceutical composition is prepared by a method including the steps of: (a) drying a plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; (e) preparing a dried MOMO30 protein composition therefrom; (f) adding one or more pharmaceutically acceptable carriers to the dried MOMO30 protein composition, and (g) forming a pharmaceutically acceptable oral composition therefrom in the form of a powder, capsule, tablet, or liquid. The composition resulting therefrom is substantially free of plant components less than 10 kDa in size, and includes a protein of about 30 kDa in size that is stable after boiling at 100° C. for 20 min, that binds HIV gp120, and that comprises the amino acid sequence of SEQ ID NO: 1.

In certain preferred embodiments, the plant comprising MOMO30 protein is a member of the *Momordica* genus. In a more particular embodiment, the plant is *Momordica balsamina*.

In some embodiments, the clarified plant cell lysate is passed through a 30-50 kDa molecular weight cut-off filter prior to preparing the dried MOMO30 protein composition. In other embodiments, the clarified plant cell lysate is subjected to immunoaffinity purification using an anti-MOMO30 antibody prior to preparing the dried MOMO30 protein composition for oral administration.

In some embodiments, the pharmaceutical composition is administered in the form of a powder. In other embodiments, the pharmaceutical composition is administered in the form of a capsule or tablet. In yet other embodiments, the pharmaceutical composition is administered in the form of a liquid.

In another aspect, the present application comprises a MOMO30 protein. In another embodiment, the composition comprises a nucleic acid encoding or operatively linked to express a MOMO30 protein. In preferred embodiments, the MOMO30 protein is derived from a plant species of the *Momordica* genus.

A particularly preferred species is *Momordica balsamina*.

In another aspect, a method for preventing or treating a viral infection comprises administering to a subject in need thereof, a MOMO30 protein or MOMO30-encoded nucleic acid by in vivo or ex vivo gene therapy.

BRIEF DESCRIPTION OF THE DRAWINGS

FIG. 7 shows an exemplary process for producing an aqueous plant extract from dried *Momordica balsamina* leaves.

FIG. 14B shows an increase in CD4+ lymphocytes following treatment with the MOMO30 plant extract.

In FIG. 15C, a subset of the originally treated patients (n=13) were re-tested at 180 months. The results of this analysis showed that CD4 counts in most of the re-tested patients returned to near baseline levels. In addition, viral loads in ten of these re-tested patients had decreased to undetectable (<20 copies/ml); two patients had very low levels (~3000 copies/ml) and one was reported as (20 copies/ml) at 180 months post-treatment.

FIGS. 16A-16B shows that the 13 re-tested patients in FIG. 14C produced neutralizing antibodies. FIGS. 16A and 16B show the results of patients' serum being tested for neutralizing activity against HIV-1 pseudotyped with an NL4-3 env or an aMLV env, respectively.

FIG. 16C shows a table depicting examples of antibody titers against 10 primary strains and 3 lab strains of HIV-1. The table summarizes reciprocal dilutions of the inhibitory dose to induce 50% reduction in replication of virus (ID 50). Darker shaded areas depict higher titers, while the lighter shaded areas depict lower titers.

FIG. 18A shows the N-terminal sequence of MOMO30 as determined by Edman degradation. FIG. 18B shows the top ten hits when the N-terminal sequence was compared to the NR database by BLAST (light blue). FIG. 18C is a western blot showing detection of a 30 kDa protein from a *M. balsamina* plant extract using a rabbit polyclonal antibody directed against the N-terminal amino acids of the MOMO30 protein in panel A. FIG. 18D shows that the anti-MOMO30 antibody blocked the ability of MOMO30 to inhibit HIV-1 infection in a dose-dependent manner (from 0.5 μg to 5.0 μg).

Figure 1A:
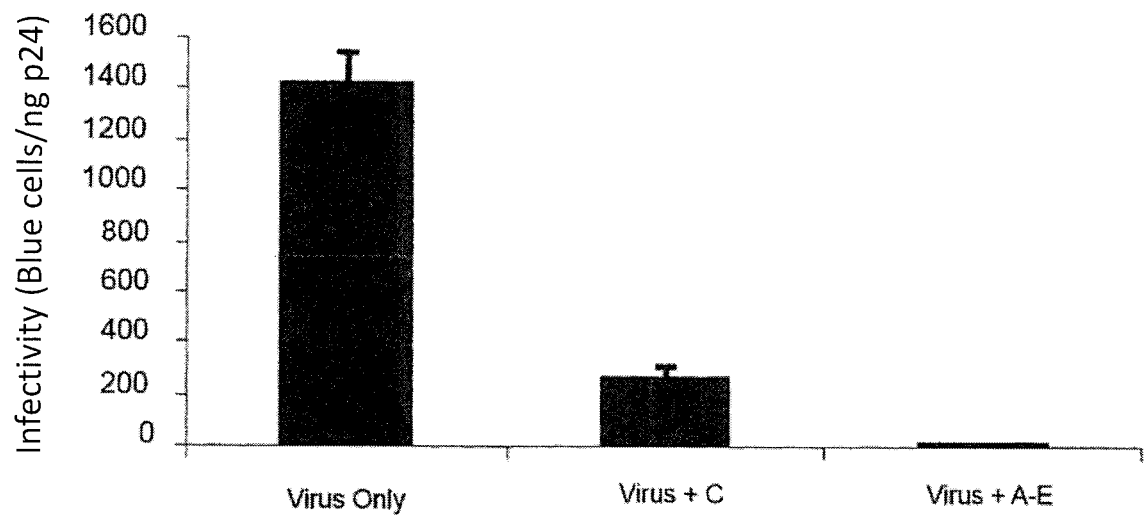
FIG. 1A shows inhibition of infectivity by HIV-1 (NL4-3) in the presence of plant extract C or a pooled combination of plant extracts A-E using a MAGI infectivity (or cell indicator) assay employing a MAGI cell line, i.e., a HeLa cell clone expressing human CD4 and HIV-LTR-ß gal.
Figure 1B:
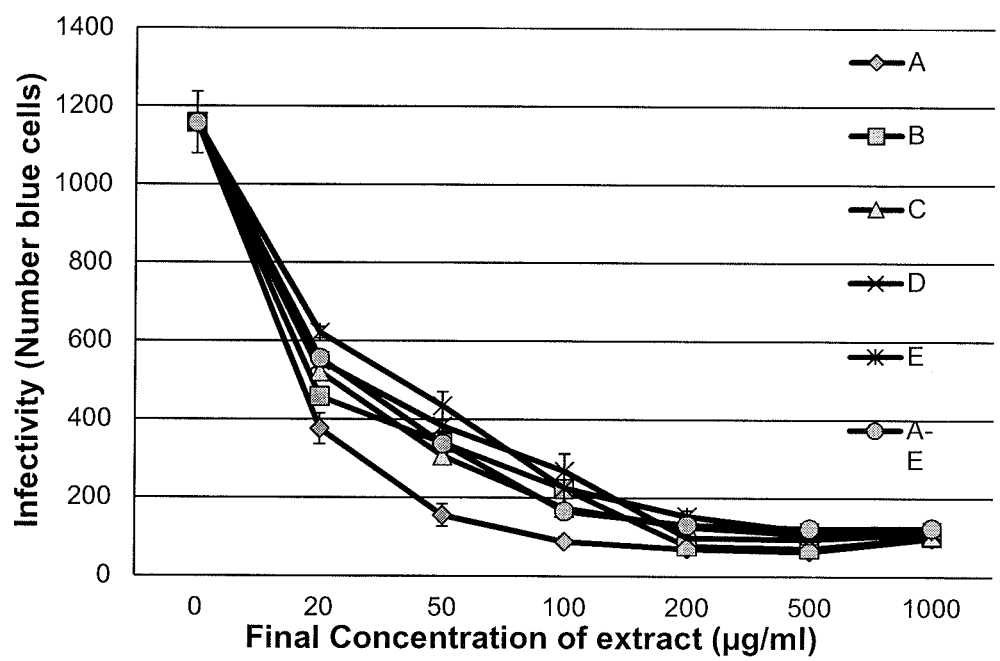
FIG. 1B shows dose response curves of the individual plant extracts in FIG. 1A or a pooled combination of plant extracts A-E shown in FIGS. 2A-B using the MAGI cell indicator assay. Extract A was prepared from *Momordica balsamina*.
Figure 2A:
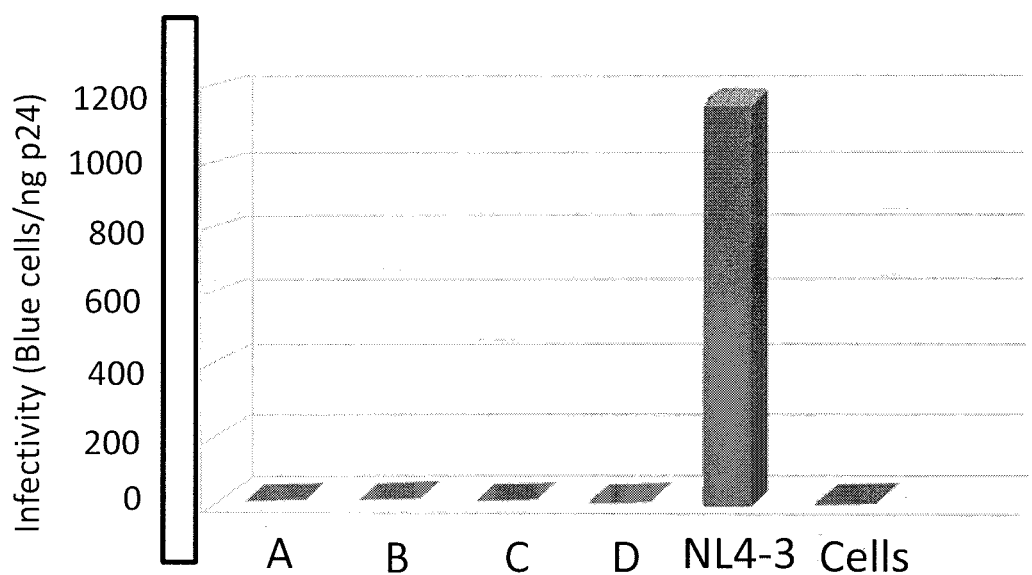
FIG. 2A shows the results of a MAGI cell indicator assay conducted with 4 independently processed plant extracts corresponding to Extract A in FIG. 1B.
Figure 2B:
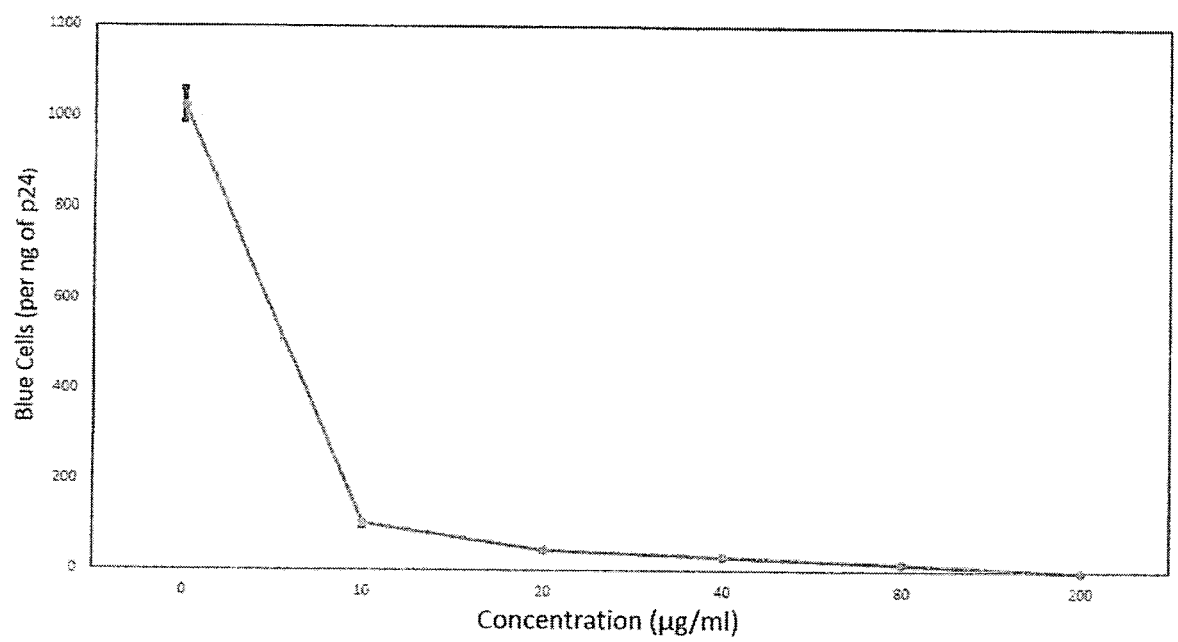
FIG. 2B is a dose response curve from a MAGI assay using an extract prepared from the second set of dried plants in FIG. 2A that was partially processed in the field with the application of heat prior to drying in order to reduce contaminants and increase potency.
Figure 3A:
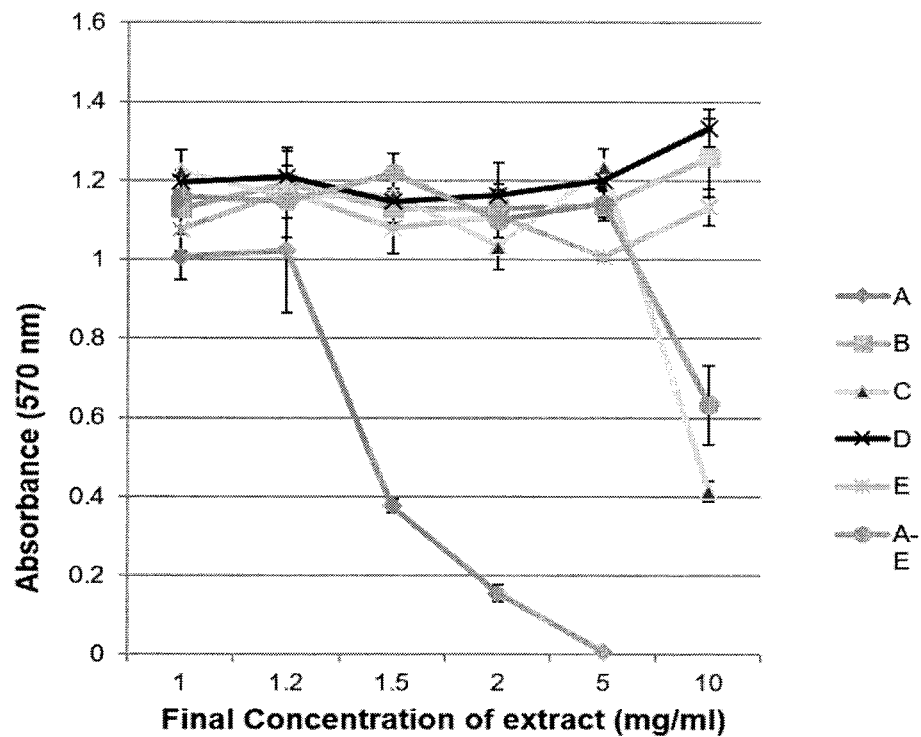
FIG. 3A shows the results of a mitochondrial toxicity test (MTT) using the plant extracts described in FIGS. 1A-B and 2A-B. Note that the X axis of this chart is in mg/ml and the infectivity assays are shown in µg/ml or 1000-fold greater.
Figure 3B:
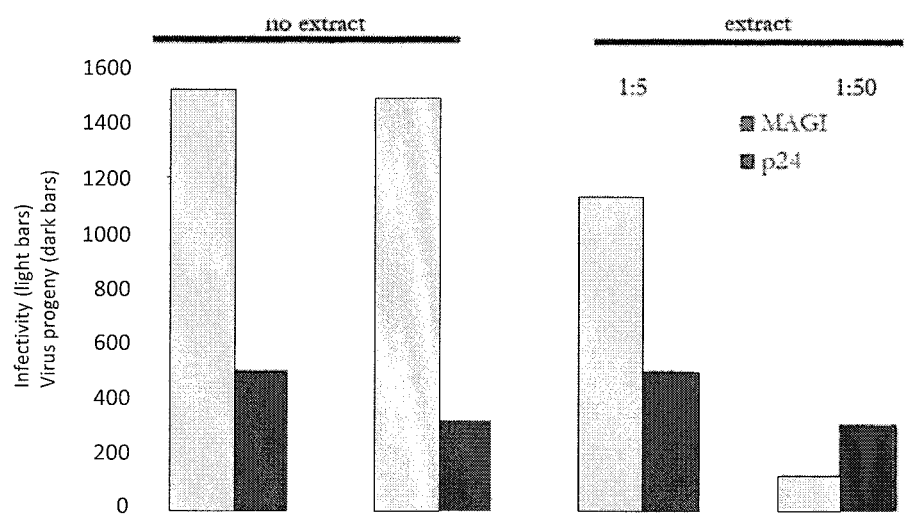
FIG. 3B shows the amount of capsid (p24) antigen produced (amount of virus) and the relative infectivity of virus (MAGI) produced by mixing infected cells with uninfected cells at a ratio of 1:5 (infected:uninfected cells) or 1:50 (infected:uninfected cells) either in the presence (left) or absence (right) of extract A.
Figures 4A, 4B:
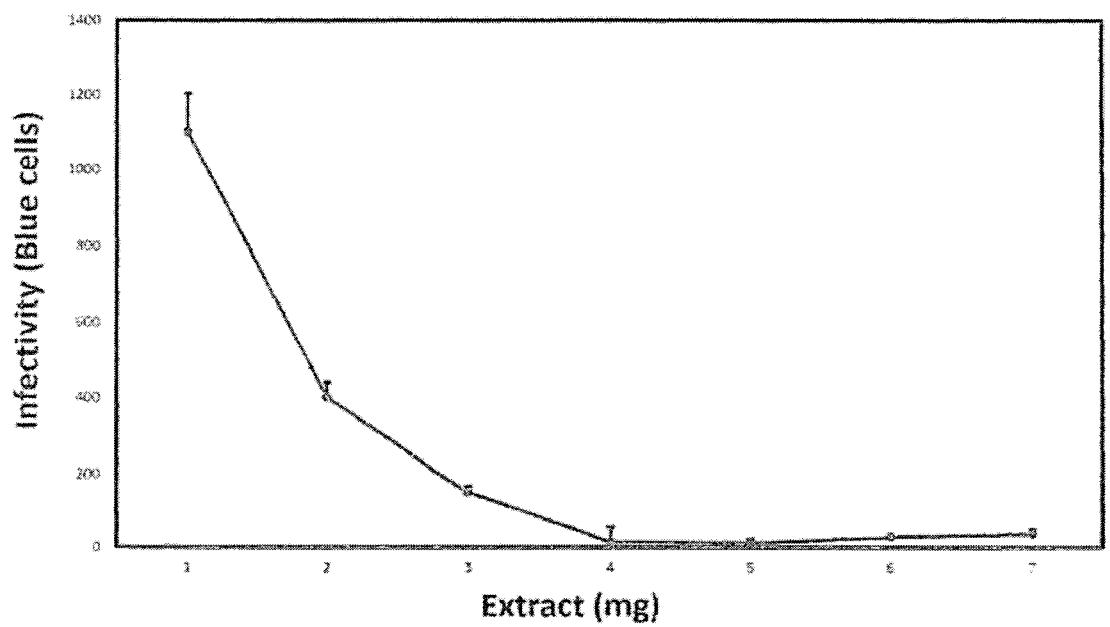
FIG. 4A shows inhibition of simian immunodeficiency virus (SIV-mac239) infectivity by plant extracts A-E described above.
FIG. 4B shows inhibition of Ebola virus (Zaire strain) infectivity in HeLa or HFF cells by the same plant extracts shown in FIGS. 1A-3B.

While the present disclosure will now be described in detail, and it is done so in connection with the illustrative embodiments, it is not limited by the particular embodiments illustrated in the figures and the appended claims.

DETAILED DESCRIPTION OF THE INVENTION

The invention and accompanying drawings will now be discussed in reference to the numerals provided therein to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art considering the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all the aspects and advantages may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but do not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used herein, the term "MOMO30 protein" is used with reference to e.g., a 30 kDa plant protein that binds gp120, is stable after boiling or autoclaving at 120° C. for 20 min, and has an HIV gp120 binding property that is sensitive to mannose. In certain preferred embodiments, the MOMO30 protein is obtained from a plant of the *Momordica* genus or a species therefrom, including *Momordica balsamina* and other species described herein, or any plant comprising a homolog thereof.

As used herein, the term "MOMO30 homolog" refers to a MOMO30-related protein that is 100%, 99.9%, 99.5%, 99%, 95%, 94%, 93%, 92%, 91%, or 90 identical to the amino acid sequence of the *Momordica balsamina* MOMO30 protein or a portion of the sequence thereof, such as SEQ ID NO: 1, or any range therefrom.

Further, it should be understood that any reference to "HIV" or "HIV-1" should be construed as applying to any isolate or clade of HIV-1 or HIV-2.

One aspect of the application is directed to MOMO30 protein, a 30 kDa plant protein that binds gp120, is stable after boiling at 100° C. for 20 min or autoclaving at 120° C. for 30 min, has a binding property that is sensitive to mannose and/or has an amino acid sequence that is 90%, 95%, 96%, 97%, 98%, 99% or 100% identical to SEQ ID NO: 1. In one embodiment, the MOMO30 is isolated from a plant of the *Momordica* genus, a species therefrom, such as *Momordica balsamina*, or any homolog thereof.

The MOMO30 product from *Momordica balsamina* is characterized by multiple properties, including: (1) a size of about 30 kDa; (2) soluble in aqueous solutions; (3) high heat resistance or high stability as reflected in no appreciable loss of activity following autoclaving at 120° C. for 30 min; (4) exhibiting mannose sensitive binding HIV gp120; (5) insensitive to digestion with trypsin following denaturation in 8M urea and overnight treatment and partially sensitive to subtilisin after overnight treatment; (6) IC50 of about 32 pM in a MAGI cell indicator assay; (7) having hemagglutinin activity; (8) capable of activating and stimulating T cell proliferation; (9) having chitinase activity; (10) capable of preventing infection by HIV-1 or alleviating symptoms in an HIV-1 infected patient; (11) having an amino terminal amino acid sequence of SEQ ID NO: 1, which is at least 93% identical to a hevamine A-like protein from *Prosopis alba*.

Without wishing to be bound by theory, MOMO30 is believed to be a carbohydrate binding agent with two distinct modes of action: (1) inhibition of virus by blocking entry into cells; (2) selecting for mutations in the viral envelope that allow the host to produce a broadly neutralizing antibody response. MOMO30 inhibits virus through binding carbohydrates. The more carbohydrates on the gp120, the more targets will be available for inhibiting virus. Under such pressure, the presence of the MOMO30 selects for virus with fewer glycosyl groups. Fewer glycosyl groups on gp120 allow more epitopes to be exposed and allows the production of neutralizing antibodies. As a consequence, patients treated with MOMO30 in the short-term exhibit the production of a broadly neutralizing antibody response. The same patients should also develop a broadly neutralizing antibody response to control their infection in the long term.

In another aspect, the present application contemplates plant homologs or variants of MOMO30 having about 80% to about 100% amino acid sequence identity to a complete MOMO30 protein sequence, including any and all whole numbers within, as well as any subranges within, wherein the lower number can be any whole number between 81% and 99% and the upper number can be any whole number between 82% and 100%.

In some embodiments, the MOMO30 protein (or homolog thereof) is encoded by a plant species of the *Momordica* genus. Exemplary *Momordica* species include, but are not limited to, *M. aculeata, M. acuminate, M. acutangula, M. adoensis, M. affinis, M. amaniana, M. angolensis, M. angulate, M. angustisepala, M. anigosantha, M. anthelmintica, M. argillicola, M. aspera, M. auriculata, M. balsamina, M. bequaertii, M. bicolor, M. boivinii, M. brachybotrys, M. bracteata, M. brevispinosa, M. bricchettii, M. cabraei, M. calantha, M. calcarata, M. camerounensis, M. cardiospermoides, M. carinata, M. casea, M. charantia, M. chinensis, M. cirrhiflora, M. cissoides, M. clarkeana, M. clematidea, M. cochinchinensis, M. cochinchinensis, M. cogniauxiana, M. cordata, M. cordatifolia, M. coriacea, M. corymbifera, M. covel, M. crinocarpa, M. cucullata, M. cylindrica, M. cymbalaria, M. dasycarpa, M. denticulata, M. denudata, M. dictyosperma, M. dioica, M. diplotrimera, M. dissecta, M. eberhardtii, M. echinata, M. echinocarpa, M. ecirrhata, M. elastica, M. elaterium, M. elegans, M. enneaphylla, M. erinocarpa, M. fasciculata, M. foetida, M. friesiorum, M. gabonii, M. garipensis, M. garriepensis, M. gilgiana, M. glabra, M. glauca, M. gracilis, M. grandibracteata, M. grosvenorii, M. guttata, M. hamiltoniana, M. hamiltoniana, M. henriquesii, M. heterophylla, M. heyneana, M. hispida, M. huberi, M. humilis, M. hystrix, M. indica, M. involucrata, M. jagorana, M. jeffreyana, M. kirkii, M. lambertiana, M. lanata, M. laotica, M. laurentii, M. leiocarpa, M. littorea, M. luffa, M. luffa, M. macrantha, M. macropetala, M. macrophylla, M. macropoda, M. macrosperma, M. maculata, M. mannii, M. marlothii, M. martinicensis, M. meloniflora, M. macrophylla, M. missionis, M. mixta, M. monadelpha, M. morkorra, M. mossambica, M. multicrenulata, M. multiflora, M. muricata, M. obtusisepala, M. officinarum, M. operculata, M. ovata, M. paina, M. palmata E, M. papillosa, M. parvifolia, M. pauciflora, M. pedata, M. pedisecta, M. peteri, M. procera, M. pterocarpa, M. punctata, M. purgans, M. pycnantha, M. quinquefida, M. quinqueloba, M. racemiflora, M. racemosa, M. renigera, M. repens, M. reticulata, M. rostrata, M. rotunda, M. roxburghiana, M. rumphii, M. runssorica, M. rutshuruensis, M. sahyadrica, M. sativa, M. schimperiana, M. schinzii, M. schliebenii, M. senegalensis,*

*M. sessilifolia, M. sicyoides, M. silvatica, M. sinensis, M. somalensis, M. sphaeroidea, M. spicata, M. spinosa, M. stefaninii, M. subangulata, M. surculata, M. suringarii, M. thollonii, M. tonkinensis, M. trifolia, M. trifoliata, M. trilobata, M. tuberosa, M. tubiflora, M. tubulosa, M. umbellata, M. verticillata, M. vogelii, M. wallichii, M. welwitschii, M. wildemaniana, M. zeylanica,* and *M. zeylanica*. In some embodiments, the MOMO30 protein may be obtained from any of the foregoing *Momordica* leaf extracts, fruit extracts, root extracts, bark extracts, seed extracts and/or any flower thereof.

In certain preferred embodiments, the MOMO30 protein is obtained from *Momordica balsamina* leaf extracts. In other embodiments, the MOMO30 protein is obtained from *Momordica balsamina* fruit extracts, root extracts, bark extracts, seed extracts and/or any flower thereof. In yet other embodiments, the MOMO30 protein is prepared from cells transformed with an expression vector encoding *M. balsamina* MOMO30 or any other MOMO30 plant source.

In other embodiments, the MOMO30 protein (or homolog thereof) is encoded by a plant species of the *Prosopis* genus. Exemplary *Prosopis* species include, but are not limited to, *P. abbreviata, P. affinis, P. african, P. alba, P. chilensis, P. cineraria, P. farcta, P. fiebrigii, P. flexuosa, P. glandulosa, P. hassleri, P. juliflora, P. laevigata, P. koelziana, P. kuntzei, P. nigra, P. pallida, P. pubescens, P. reptans, P. rojasiana, P. ruscifolia, P. spicigera, P. strombulifera, P. tamarugo,* and *P. velutina*. In some embodiments, the MOMO30 protein may be obtained from any of the foregoing *Prosopis* leaf extracts, fruit extracts, root extracts, bark extracts, seed extracts and/or any flower thereof.

In some embodiments, the MOMO30 protein is 100%, 99.9%, 99.5%, 99%, 95%, 94%, 93%, 92%, 91%, 90%, 89%, 88%, 87%, 86%, 85%, 84%, 83%, 82%, 81%, or 80% identical to the amino acid sequence of the *Momordica balsamina* MOMO30 protein or a portion of the sequence thereof, or any range therefrom.

In some embodiments, the MOMO30 protein is a variant containing one or more mutations relative to the wild-type sequence. "Variants" include protein sequences having one or more amino acid additions, deletions, stop positions, or substitutions, as compared to a wild-type protein. An amino acid substitution can be a conservative or a non-conservative substitution. Variants of MOMO30 proteins can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in a protein's properties may include those in which e.g., (i) a hydrophilic residue (e.g., S or T) is substituted for (or by) a hydrophobic residue (e.g. L, I, F, V, or A); (ii) a C or P is substituted for (or by) any other residue; (iii) a residue having an electropositive side chain (e.g. K, R, or H) is substituted for (or by) an electronegative residue (e.g., Q or D); or (iv) a residue having a bulky side chain (e.g., F) that is substituted for (or by) one not having a bulky side chain, (e.g., G).

MOMO30 mutants may be generated by random mutagenesis or site-directed mutagenesis using methods known to those of ordinary skill in the art with or without selection methodologies employing MAGI indicator cell assays, apoptosis assays and the like.

In some embodiments, the present application provides a nucleic acid encoding a MOMO30 protein of the present application. In some embodiments, the MOMO30-encoded nucleic acid is 99.9%, 99%, 95%, 94%, 93%, 92%, 91% or 90% identical to a *Momordica balsamina* MOMO30 cDNA. In certain particular embodiments, the MOMO30-encoded nucleic acid includes a codon-optimized MOMO30 nucleic acid encoding the 30 kDa *M. balsamina* MOMO30 protein.

In some embodiments, the present application provides an expression vector comprising a MOMO30-encoded nucleic acid.

In other embodiments, the present application provides a host cell transformed with a MOMO30-encoded nucleic acid or MOMO30-encoded expression vector.

In another aspect, the present application provides an extract comprising a MOMO30 protein. The extract may prepared for oral administration or parenteral administration (e.g., intravenous (IV), intramuscular (IM), subcutaneous (SC or SQ), transdermal (TD)). The extract may be in dried form or it may be in aqueous solution, with or without one or more pharmaceutically acceptable carriers. In one embodiment, the extract is an herbal extract from a natural plant source, such as *M. balsamina*. In another embodiment, the extract is a cell extract from bacterial, fungal, plant, insect, or animal cells transformed with a MOMO30 expression vector to express the protein. The transformed cells may be stably transformed or they may be transiently transformed. The extract may be prepared and its composition may be modified in accordance with any of the methods of preparation outlined below or known to those of ordinary skill in the art.

In some embodiments, the MOMO30 protein or MOMO30-containing extract may be combined with one or more nutritional supplements selected from the group consisting of minerals and metals, vitamins, salts, amino acids, fatty acids, proteins, and other pharmaceutically acceptable excipients. The nutritional supplement may be included with the MOMO30 protein or MOMO30-containing extract as in a MOMO30 formulation, or it may be separately administered therewith. Exemplary supplements include vitamin A, vitamin B1, vitamin B2, vitamin B5, vitamin B6, vitamin B12, vitamin C, magnesium citrate, vitamin E, vitamin D3, calcium, zinc citrate, selenium, manganese gluconate, copper gluconate, copper gluconate, Coenzyme Q, biotin, folate, acetyl-L-carnitine, chromium polynicotinate, citrus bioflavinoids, glucosamine sulfate, boron sulfate, and whey protein. Exemplary fatty acids may be selected from the group consisting of linoleic acid (LA), gamma linoleic acid (GLA), eicosapentaneoic acid (EPA), docosapentaneoic Acid (DPA), docosahexaenoic acid (DHA), and D-alpha-tocopherol.

Alternatively, or in addition, in some embodiments, the MOMO30 protein or MOMO30-containing extract may be combined with one or more MOMO30 homologs, plant extracts and/or or plant substances to form a MOMO30 combination formulation. Exemplary plant extracts or MOMO30 homologs in such combination formulations may be obtained from one or more members selected from the group consisting of *Acacia arabia, Afromomum melegueta, Agrimonia eupatoria, Ajuga decumbens, Allium cepa, Allium sativum, Aloe vera, Alternanthera philoxeroides* or *sessiles, Ammi maius, Andographis paniculata, Apium graveolens, Apium leptophyllum, Arachis hypogaea, Arctium lappa, Artemesia Judaica, Amebia euhcroma, Asparagus racemosus, Astragalus spinosus, Astragalus lentingosis swainsonine, Azadirachta indica, Balanites aegyptiaca, Bauhinia rufescens, Bersama tysoniana, Blumea alata, Brucea antidysenterica, Buchenavia capita, Butyrospermum parkii, Bryonia cretica* ssp. *Dioica, Bryonia angustifolia, Calotropis procera, Camellia theifera, Camellia sinensis, Casia sieberiana, Catha edulis. Cedrela toona, Chrysanthemum morifolium, Clausena anisata, Clivia miniata, Cochlospermum planchonii, Coffea arabica, Cola nitida, Combretum glutinosum, Combretum micranthum, Coptis chinesis, Coptis teetoides, Coptis japonica, Coraria nepalensis, Coriandrum sativum, Cryptolepis sanguinolenta, Curcuma longa, Cyperus articulatus, Cyperus domestus, Cyperus rigidifolius, Datura metel syn alba, Daucus carota, Diospyros mespiliformis, Echinacea angustiflora and purpurea, Echinacea simulata, Echinacea pallida, Entada abyssinica, Epimedium grandiflorum, Epimedium sagittatum, Epimedium sinense, Epilobium angustifolium, Erigeron Canadensis, Eugenia or Syzigium claviflorum, Euphorbia hirta, Faidherbia albida, Fagara xanthox, Ficus iteophylla, Ficus platphylla, Foeniculum vulgarel, Garcinia afzelii, Garcinia epundata, Gardenia coronaria, Gaultheria trichophylla, Glycine max, Glycyrrhiza labra, Gossypium herbaceum, Guiera senegalensis, Heracleum sphondylium, Hypericum perforatum, Hypericum japonicum, Hyssopus officinalis, Jasminum officinale, Khaya senegalensis, Lippia javanica, Lithospermum erythrorhizon, Lonicera japonica, Lophira lanceolate, Luffa, Lycopus europaeus, Magnolia officinalis, Mallotus repandus, Mallotus philippinesis, Matricaria chamomil, Matricaria recutitia, Melissa parviflora, Melissa officinalis, Momordica* species, including *Momordica balsamina, Momordica charantia* and others; *Morinda lucida, Narcissus tazetta, Narcissus pseudonarcissus, Ocimum gratissimum, Oenthera rosea, Paeonia* spec., *Papaver somniferum, Parkia biglobosa, Perilla frutescens, Persea Americana, Phyllanthus niruri, Pinus koraicenis, Pinus parviflora, Piper nirgum, Plumeria rubra, Polyantha suberosa, Prosopis* sp., including *P. africana* and others; *Prunus africans, Prunella vulgaris, Prunus bakariensis, Prunus amygdalus, Psoralea corylifolia, Randia dunatorum, Raphanus sativus, Rheum palmatum, Rhus coriaria, Rhus chinesis, Ricinus communis, Rosmarinus officinalis, Salic mucronata, Salvia miltiorhiza* and *officinalis, Salvadora persica, Sambucus ebulus, Saussurea lappa, Scilla griffithii, Scutellaria baicalensis baiealein, Sedum sediforme, Senecio scandens, Senecio aereus, Senna alata, Silybum marianum, Skimmia laureola, Solarium niporum, Swertia franchetiana, Tamarindus indica, Terminalia alata, Terminalia catappa, Terminalia chebula, Terminalia glaucescens, Thula occidentalis, Trapalaponica* spec., *Trichosanthes dioica, Trichosanthes kirilowii, Urtica dioica, Viola yeodensis, Vitellaria paradoxa, Voacanga africana, Woodfordia fruticosa, Woodwardia* spec., *Zanoxylum nitidum, Zanthoxylum zanthoxyloides*, and *Ziziphus mauritania*, including powder or extract from leaf, bark, seed, root, and/or flower therefrom.

In one embodiment, the MOMO30 combination formulation includes one or more plant extracts selected from the group consisting of *Momordica balsamina, Aframomum melegueta, Cyperus domestus, Ficus iteophylla* and *Tamarindus indica*. In another embodiment, the MOMO30 combination formulation includes one or more plant extracts selected from the group consisting of *Momordica balsamina, Aframomum melegueta, Cyperus articulatus, Ficus iteophylla* and *Tamarindus indica*. In another embodiment, the MOMO30 combination formulation includes one more plant extracts selected from the group consisting of *Momordica balsamina, Aframomum melegueta* and *Cyperus articulatus*. In a more particular embodiment, the MOMO30 combination formulation includes a leaf extract from *Momordica balsamina*, a seed extract from *Aframomum melegueta* and/or a root extract from *Cyperus articulatus*.

Exemplary plant-derived substances include lentinan, a polysaccharide isolated from the fruit body of shiitake mushroom (*Lentinula edodes* mycelium) and various ribosome inactivating proteins (RIPs) from *M. balsamina* and *Trichosanthis kirilowii*, such as Momordin I and Momordin II, as well as ribosome inactivating proteins from any of the foregoing plant extracts. It is believed that the addition of the aforementioned nutritional supplements and/or plant-based substances may be further increase the prophylactic and/or therapeutic efficacy of the MOMO30 protein, especially in patients with HIV or any of the other viral infections described herein below.

Another aspect of the application is a method of preparing a MOMO30-containing plant extract, including but not limited to plants of the *Mormordica* genus, such as *Momordica balsamina*. In one embodiment, the method includes one or more steps including: harvesting the plants; drying the plants; extracting the dried plants in water or aqueous media; collecting the plant cells by centrifugation; lysing or disrupting the plant cell membranes by physical or chemical means; centrifuging the plant cell lysate to remove debris and particulates; filtering the clarified plant cell lysates by e.g., running the lysate through a molecular weight cutoff (MWCO) filter (e.g., Amicon 30 kDa or 50 kDa); eluting the semi-purified extract from the retentate; drying the semi-purified extract or resuspending the semi-purified extract in buffer for further analysis, purification and/or storage. The MOMO30 protein may be further purified from the plant extract by immunoaffinity chromatography and other conventional methodologies known to those of skill in the art.

In a particular embodiment, a method for preparing a partially purified MOMO30-containing plant extract comprises the steps of: (a) forming an aqueous plant extract from one or more dried plant leaves comprising MOMO30 protein; (b) lysing the plant cells; (c) centrifuging the aqueous plant extract to remove debris and particulates; (d) retaining the aqueous supernatant; (e) filtering the aqueous supernatant through a MW cutoff filter and/or subjecting the supernatant to immunoaffinity purification; and (f) eluting MOMO30 into buffer for storage and/or use. In certain embodiments, the MOMO30 protein may be dried for storage or resuspended in an appropriate buffer for further use or storage following e.g., quantification of MOMO30 yield and/or characterization of MOMO30 purity. In practice, the extracts are quite stable and have been stored freeze dried for years without significant loss of anti-viral activity.

In addition, the extract, purified extract and/or purified MOMO30 protein may be characterized by HPLC and/or tested for functional activity via infectivity assays and the like. For example, in some embodiments, the MOMO30-containing plant extract or purified protein may be evaluated for functional activity by testing their ability to inhibit infection by HIV using a MAGI cell infectivity assay (or "indicator assay"). This assay involves the use of genetically modified CD4-expressing HeLa cell line (MAGI) containing an HIV LTR-driven cassette placed upstream of the E. coli β-gal encoded reporter gene (HeLa-CD4-LTR-β-gal). See Kimpton and Emerman, J Virol 66:2232, 1992. Expression of the reporter gene is activated in the presence of HIV Tat, which is expressed upon infection by HIV, such as HIV-1 (NL4-3) and activates the HIV-1 LTR. Cells infected by HIV turn blue and can be counted under a microscope.

In certain preferred embodiments, the plant leaves comprising MOMO30 protein are obtained from members of the *Momordica* genus. In a more particular embodiment, the plant leaves are obtained from the *Momordica balsamina* plant.

Methods of Treatment

In another aspect, the present application provides a method for preventing or treating a viral infection. In one embodiment, the method comprises administering to a subject in need thereof a MOMO30 protein or MOMO30-containing composition or combination formulation according to the present application to prevent a viral infection. In another embodiment, the method comprises administering to a virally infected subject in need thereof a MOMO30 protein or MOMO30-containing extract or formulation according to the present application to reduce the symptoms associated with the viral infection or cure the subject of the disease.

In another embodiment, the present application provides a method for treating a viral infection. In another embodiment, the method comprises administering to a subject in need thereof a MOMO30 protein, a MOMO30 containing extract or combination formulation, or MOMO30-encoded nucleic acid. The MOMO30 protein may be administered as a substantially purified protein or MOMO30-encoded nucleic acid in a pharmaceutically acceptable carrier, alone or in combination with a suitable adjuvant, or it may be administered as plant extract alone or in combination with other nutritional supplements, plant extracts or plant components described above.

In another embodiment, the method of treatment further comprises administering to the subject in need thereof a MOMO30 protein, a MOMO30 containing extract or combination formulation, or MOMO30-encoded nucleic acid prepared by any of the processes described herein.

The method may be used to prevent or treat any infection that is inhibited by the MOMO30 protein or MOMO30-encoded expression vector, including but not limited to enveloped RNA and DNA viruses, including RNA viruses, such as retroviruses, alphaviruses, bunyaviruses, coronaviruses, filoviruses, flavivirus, hepatitis viruses, orthomyxoviruses (e.g., influenza Types A, -B, -C, -D), paramyxoviruses, rhabdoviruses, and togaviruses; and DNA viruses, such as herpesviruses, poxviruses, and hepadnaviruses. Preferably, the virus includes an envelope containing mannose residues.

Exemplary species of enveloped viruses for prophylactic or therapeutic use, include human immunodeficiency virus type 1 and type 2 (HIV-1 and HIV-2), human T-cell lymphotropic virus type I and type II (HTLV-I and HTLV-II), hepatitis B virus (HBV), hepatitis C virus (HCV), hepatitis delta virus (HDV), hepatitis E virus (HEV), hepatitis G virus (HGV), hepatitis A virus, hepatitis G virus, hepatitis E virus, transfusion transmitted virus (TTV), Epstein-Barr virus, human cytomegalovirus type 1 (HCMV-1), human herpes virus type 6 (HHV-6), human herpes virus type 7 (HHV-7), human herpes virus type 8 (HHV-8), influenza type A virus, including subtypes H1N1 and H5N1, as well as types-B, -C, and -D, severe acute respiratory syndrome (SARS) coronavirus, and RNA viruses that cause hemorrhagic fever, such as Filoviridae (e.g., Ebola virus (EBOV) and Marburg virus (MBGV)); Bunyaviridae (e.g., Rift Valley fever virus (RVFV) and Crimean-Congo hemorrhagic fever virus (CCHFV)); and Flaviviridae (West Nile virus (WNV), Dengue fever virus (DENV), yellow fever virus (YFV), and (GB virus C (GBV-C), formerly known as Hepatitis G virus (HGV), and the like.

Route and Dose of Antiviral Product Administration

An antiviral MOMO30 product of the present application may be administered orally, intrathecally, intra-arterially, intravenously, intradermally, subcutaneously, transdermally (topically) or transmucosally. An antiviral composition may be administered by any route, including oral, rectal, pulmonary, sublingual, and parenteral administration. Parenteral administration includes, for example, intraperitoneal, intravenous, intramuscular, intraarterial, intravesical (e.g., to the bladder), intradermal, transdermal, topical, or subcutaneous administration.

As a general proposition, the therapeutically effective amount of an antiviral MOMO30 product administered will be in a weight range of about 1 ng/kg body weight/day to about 100 mg/kg body weight/day whether by one or more administrations. In more particular embodiments, the antiviral MOMO30 product or MOMO30-containing formulation is administered in weight range from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, an antiviral MOMO30 product is administered at a dosage range of 1 ng-10 ng per injection, 10 ng-100 ng per injection, 100 ng-1 µg per injection, 1 µg-10 µg per injection, 10 µg-100 µg per injection, 100 µg-1 mg per injection, 1 mg-10 mg per injection, 10 mg-100 mg per injection, and 100 mg-1000 mg per injection. The MOMO30 protein or MOMO30-containing formulation may be injected once daily, twice daily, three times daily, and/or every 2, 3, 4, 5, 6 or 7 days. In addition, the MOMO30 protein or MOMO30-containing formulation may be administered over a period of one month, two months, six months, 12 months, 2 years, 5 years, 10 years, 20 years, or more.

In other embodiments, the antiviral MOMO30 product or MOMO30-containing formulation may be administered in a range from about 1 ng/kg to about 100 mg/kg. In more particular embodiments, the antiviral MOMO30 product or MOMO30-containing formulation may be administered in a range from about 1 ng/kg to about 10 ng/kg, about 10 ng/kg to about 100 ng/kg, about 100 ng/kg to about 1 µg/kg, about 1 µg/kg to about 10 µg/kg, about 10 µm/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antiviral MOMO30 product administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

Concentrations or amounts of MOMO30 protein may be determined using anti-MOMO30 antibodies as further described herein below. The specific dose of antiviral MOMO30 product may be determined based on the particular circumstances of the individual patient including the size, weight, age and sex of the patient, the nature and stage of the disease, the aggressiveness of the disease, and the route of administration of the antiviral composition.

In certain embodiments, an antiviral MOMO30 product or MOMO30-containing formulation may be administered at least once per day, typically once, twice, three times or four times per day with the doses given at equal intervals throughout the day and night in order to maintain a constant presence of the drug in order to provide sufficient antiviral activity. However, a skilled artisan will appreciate that a treatment schedule can be optimized for any given patient, and that administration of compound may occur less frequently than once per day.

In other embodiments, an antiviral MOMO30 product or MOMO30-containing formulation of the present application is prescribed to be taken in combination with other antiviral agents and/or the other active agents described above. Examples of other antiviral agents include, but are not limited to, antibiotics, other antiviral peptides, and in vivo expression vectors that encode an antiviral MOMO30 product of the present application. When used in such combinations, the antiviral MOMO30 product of the present application and other antiviral agents may be administered simultaneously, by the same or different routes, or at different times during treatment.

The treatment may be carried out for as long a period as necessary, i.e., until the infection is cleared or no longer a threat to the host. In some cases, the treatment may be continued indefinitely while the disease state persists, although discontinuation might be indicated if the antiviral compositions no longer produce a beneficial effect. In one embodiment, the treatment is carried out for 6 months and then discontinued. The treating physician can determine whether to increase, decrease, or interrupt treatment based on a patient's response, including evaluation of immune responses, viral loads etc.

An antiviral MOMO30 product of the present application can be chemically synthesized or produced from cells transformed with polynucleotide expression vectors encoding a MOMO30 gene using recombinant DNA technologies well known to those skilled in the art. Polynucleotide expression vectors can be designed to facilitate preparative expression levels in many different cell hosts, including bacteria, yeast, insect cells, and mammalian cells.

In some microorganisms, such as wild type *E. coli*, the periplasm constitutes an oxidizing environment, whereas the cytoplasm is a reducing environment. Accordingly, expression in the *E. coli* periplasm may enable the production of peptides containing interchain or intrachain disulfide bonds that might be otherwise reduced in cytoplasm, where it may be toxic to the cell. Some prokaryotic organisms have endogenous, intracellular oxidizing environments and can normally accommodate formation of protein disulfide bonds inside the cell. Accordingly, the fusion protein may be periplasmically expressed using an operably linked periplasmic signal sequence at the 5' end of the corresponding nucleic acid expression construct.

The MOMO30 product may be fused to other protein domain, including binding tags conferring additional biochemical properties, targeting properties, antiviral properties etc. When fused to another protein domain in an expression vector, the MOMO30 encoded product in the expression vector may further include a cleavage recognition site for proteolytic cleavage of one or more peptide domains from one another. The cleavage recognition sequence can be cleaved by a suitable protease, such as Kex2p or furin, at one or more defined residues.

Where the cleavage recognition site is positioned adjacent to an adjacent protein domain, proteolytic cleavage in a transduced cell can liberate one or more antiviral domains from one another so that the antiviral products can function independently of one another according to their designated microbial cell surface target or microbial intracellular target.

For example, when positioned in or adjacent to a spacer region adjacent to the MOMO30 gene product, the expressed peptide can be directly cleaved when introduced into a microbial cell bearing the corresponding protease. In one embodiment, the proteolytic recognition site is a Kex2p-sensitive proteolytic cleavage site. In another embodiment, the proteolytic recognition site is the furin proteolytic cleavage site, which is sensitive to cleavage by the enzyme, furin.

An expression construct can further include a native or non-native N-terminal signal peptide region to facilitate entry of the encoded antiviral MOMO30 product into the secretory pathway following gene transfer into eukaryotic cells near a site of infection.

Expression Vectors

In certain embodiments, an expression vector encoding the antiviral MOMO30 protein of the present application is directly administered to a patient to express an antiviral MOMO30 protein in vivo. In certain particular embodiments, a recombinant polynucleotide operatively linked to suitable regulatory elements for expression of a MOMO30 protein is codon optimized for expression in a selected prokaryotic or eukaryotic host cell, such as a mammalian, plant or insect cell. To facilitate replication and expression, the polynucleotide can be incorporated into a vector, such as a prokaryotic or a eukaryotic expression vector. Suitable non-viral expression vectors include, but are not limited to, plasmid expression vector or a bacteriophage vectors. Suitable viral vectors include, but are not limited to, retroviral vectors, lentiviral vectors, adenoviral vectors, adeno-associated viral (AAV) vectors, herpes viral vectors, and alphavirus vectors. The viral vector can also be an astrovirus, coronavirus, orthomyxovirus, papovavirus, paramyxovirus, parvovirus, picornavirus, poxvirus, togavirus viral vector.

The term "in vivo expression vector" refers to a non-viral or viral vector that comprises a polynucleotide encoding an antiviral MOMO30 protein of the present application in a form suitable for expression of the polynucleotide in a host cell. The expression vectors include one or more regulatory sequences, selected on the basis of the host cells to be used for expression, and operably linked to the polynucleotide sequence to be expressed. It will be appreciated by those skilled in the art that the design of the expression vector can depend on such factors as the choice of the host cell to be transformed, the level of expression of protein desired, and the like. The expression vectors can be introduced into host cells to produce an antiviral MOMO30 protein of the present application.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences). An expression vector may be designed to facilitate expression of an antiviral MOMO30 protein-encoding polynucleotide in one or more cell types. Tissue-specific regulatory elements may be used to restrict expression to a particular cell type.

A nucleic acid sequence is "operably linked" to another nucleic acid sequence when the former is placed into a functional relationship with the latter. For example, a DNA for a presequence or secretory leader peptide is operably linked to DNA for a protein if it is expressed as a preprotein that participates in the secretion of the protein; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

Delivery of antiviral MOMO30 protein-encoding expression vectors can be achieved by infection (for viral vectors), transfection (for non-viral vectors) and other methods well known to one skilled in the art. Examples of other delivery methods and media include, polycationic condensed DNA linked or unlinked to killed viruses, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may also be employed.

Plasmid DNA expression vectors can be utilized for non-viral gene transfer, either by direct injection of naked DNA or by encapsulating an antiviral MOMO30 protein-encoding polynucleotide in liposomes, microparticles, microcapsules, virus-like particles, or erythrocyte ghosts. Such compositions can be further linked by chemical conjugation to, for example, microbial translocation domains and/or targeting domains to facilitate targeted delivery and/or entry of nucleic acids into the nucleus of desired cells to promote gene expression. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin. Naked DNA may also be employed. Uptake efficiency of naked DNA may be improved using biodegradable latex beads. Such delivery may be improved further by treating the beads to increase hydrophobicity and thereby facilitate disruption of the endosome and release of the DNA into the cytoplasm.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers and silencers) which regulate activation or repression of genes operably linked thereto in response to developmental and/or external stimuli and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

Examples of such promoters include: the immediate early promoter of CMV, LTR or SV40 promoter, polyhedron promoter of baculovirus, *E. coli* lac or trp promoter, phage T7 and lambda PL promoter and other promoters known to control expression of genes in prokaryotic or eukaryotic cells or their viruses. The expression vector typically also contains a ribosome binding site for translation initiation and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture or such as tetracycline or ampicillin resistance in *E. coli*.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a protein coding sequence or a portion thereof, is inserted, exogenous translational control signals, including an ATG initiation codon is provided for expression of an antiviral MOMO30 protein. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. (1994) Results Probl Cell Differ 20:125-62; Bitter et al. (1987) Methods in Enzymol 153:516-544).

Expression vectors carrying an antiviral MOMO30-encoding nucleic acid can be introduced into host cells by any of a variety of well-known procedures, such as electroporation, liposome mediated transfection, calcium phosphate precipitation, infection, transfection and the like, depending on the selection of vectors and host cells.

Host cells that contain antiviral MOMO30 protein-encoding nucleic acids are, thus, also a feature of this disclosure. Favorable host cells include prokaryotic (i.e., bacterial) host cells, such as *E. coli*, as well as numerous eukaryotic host cells, including plant (e.g., tobacco), fungal (e.g., yeast, such as *Saccharomyces cerevisiae* and *Picchia pastoris*) cells, insect cells, and mammalian cells (such as CHO cells). Recombinant antiviral MOMO30-encoding nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as *E. coli, Streptomyces* and *Salmonella typhimurium*; fungal cells, such as *Saccharomyces cerevisiae, Pichia pastoris* and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants or amplifying the inserted polynucleotide sequences. The culture conditions, such as temperature, pH and the like, are typically those previously used with the host cell selected for expression and will be apparent to those skilled in the art.

In bacterial systems, a number of expression vectors can be selected depending upon the use intended for the expressed product. For example, when large quantities of a protein or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with e.g., sequences for the amino-terminal translation initiating methionine and the subsequent 7 residues of beta-galactosidase producing a catalytically active beta galactosidase fusion protein in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number of expression systems, including both plasmids and viral-based systems, can be utilized.

A host cell is optionally chosen for its ability to modulate the expression of the inserted sequences or to process the expressed protein in the desired fashion. Such modifications of the protein include, but are not limited to, glycosylation, acetylation, carboxylation, phosphorylation, lipidation, acylation etc. Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant antiviral MOMO30 protein, stable expression systems may be employed. For example, polynucleotides encoding an antiviral MOMO30 protein can be introduced into suitable host cells using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding an antiviral MOMO30 protein are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted protein product is then recovered from the culture medium. Alternatively, cells can be harvested by centrifugation, disrupted by physical or chemical means and the resulting crude extract retained for further purification. Eukaryotic or microbial cells employed in expression of proteins can be disrupted by any convenient method, including freeze-thaw cycling, sonication, mechanical disruption or use of cell lysing agents or other methods, which are well known to those skilled in the art.

Expressed antiviral MOMO30 proteins can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography and lectin chromatography. Since the MOMO30 protein is unusually heat stable it also suggests that application of heat to denature other proteins may be a useful approach. Protein refolding steps can be used, as desired, in completing configuration of the mature protein. Finally, high performance liquid chromatography (HPLC) can be employed in the final purification steps.

In certain examples, the nucleic acids are introduced into vectors suitable for introduction and expression in prokaryotic cells, e.g., *E. coli* cells. For example, a nucleic acid including a polynucleotide sequence that encodes a F2GF1 chimeric RSV antigen can be introduced into any of a variety of commercially available or proprietary vectors, such as the pET series of expression vectors (e.g., pET19b and pET21d). Expression of the coding sequence is inducible by IPTG, resulting in high levels of protein expression. The polynucleotide sequence encoding the chimeric RSV antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode F2GF1 chimeric RSV antigens.

In another example, a polynucleotide sequence that encodes an antiviral product is introduced into insect cells using a baculovirus expression vector system (BEVS). Recombinant baculovirus capable of infecting insect cells can be generated using commercially available vectors, kits and/or systems, such as the BD BaculoGold system from BD BioScience. Briefly, the polynucleotide sequence encoding the antiviral product is inserted into the pAcSG2 transfer vector. Then, host cells SF9 (*Spodoptera frugiperda*) are co-transfected by pAcSG2-chimer plasmid and BD Baculo- Gold, containing the linearized genomic DNA of the baculovirus Autographa californica nuclear polyhedrosis virus (AcNPV). Following transfection, homologous recombination occurs between the pACSG2 plasmid and the Baculovirus genome to generate the recombinant virus. In one example, the antiviral product is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the SF9 and the High Five (Hi5) cell line derived from a cabbage looper, Trichoplusia ni.

Following transfection and induction of expression (according to the selected promoter and/or enhancers or other regulatory elements), the expressed proteins are recovered (e.g., purified or enriched) and renatured to ensure folding into a biologically active conformation.

In yet other embodiments, the antiviral products are expressed in vivo using viral or non-viral expression vectors.

Viral-based expression vectors. In some embodiments, antiviral product or siRNA encoding sequences (or shRNAs) are delivered from viral-derived expression vectors. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers and can be delivered in aerosol formulation and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promoter cassette being inserted into the viral genome in place of the removed viral DNA. The necessary functions of the removed gene(s) may be supplied by cell lines which have been engineered to express the gene products of the early genes in trans.

Non-viral expression vectors. In other embodiments, non-viral delivery systems are utilized for delivery of plasmid vectors or other bioactive non nucleic acid agents using lipid formulations comprising, for example, liposomes, such as cationic liposomes (e.g., DOTMA, DOPE, DC-cholesterol) and anionic liposomes. Liposomes can be further conjugated to one or more proteins or peptides to facilitate targeting to a particular cell, if desired. Administration of a composition comprising a compound and a cationic liposome can be administered to the blood afferent to a target organ or inhaled into the respiratory tract to target cells of the respiratory tract. Furthermore, active agent(s) can be administered as a component of a microcapsule or nanoparticle that can be targeted to a cell type of interest using targeting moieties described herein or that can be designed for slow release of one or more active agent(s) in accordance with a predetermined rate of release or dosage.

In other embodiments, the nucleic acids may be delivered in vivo by electroporation, the technology for which is available from Genetronics, Inc. (San Diego, Calif.), as well as by means of a SONOPORATION machine (ImaRx Pharmaceutical Corp., Tucson, Ariz.).

The nucleic acids may be in solution or suspension (for example, incorporated into microparticles, liposomes or cells). These may be targeted to a particular cell type via antibodies, receptors or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted and then either recycle to the cell surface, become stored intracellularly or are degraded in lysosomes. The internalization pathways serve a variety of functions, such as nutrient uptake, removal of activated proteins, clearance of macromolecules, opportunistic entry of viruses and toxins, dissociation and degradation of ligand and receptor level regulation. Many receptors follow more than one intracellular pathway, depending on the cell type, receptor concentration, type of ligand, ligand valency and ligand concentration.

Pharmaceutical Compositions

As used herein the language "pharmaceutically acceptable carrier" is intended to include any and all solvents, solubilizers, fillers, stabilizers, binders, absorbents, bases, buffering agents, lubricants, controlled release, vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the application is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an antiviral peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and poly lactic acid. Methods for preparation of such formulations will be apparent to those skilled in the art. The materials can also be obtained commercially from e.g., Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the present application are dictated by and directly dependent on the unique characteristics of the active compound and the particular therapeutic effect to be achieved, and the limitations inherent in the art of compounding such an active compound for the treatment of individuals.

Toxicity and therapeutic efficacy of the antiviral product of the present application can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present application, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present application is further illustrated by the following examples that should not be construed as limiting. The contents of all references, patents, and published patent applications cited throughout this application, as well as the Figures and Tables, are incorporated herein by reference.

EXAMPLES

In one aspect, the present application is directed to a 30 kDa broad-spectrum antiviral protein product from plants, such as *Momordica balsamina*. As further described below, the active antiviral protein was characterized as a heat-stable, gp120-binding antiviral protein of about 30 kDa in size, which is otherwise referred to as the "MOMO30" protein.

Preparation and Inhibitory Activity of MOMO30 Protein

The functional activity of the MOMO30 protein was originally assayed from *Momordica balsamina* plant extracts prepared according to the steps outlined in FIG. 1, as further described above. FIG. 1 shows an exemplary method for preparing a partially purified MOMO30-containing plant extract from e.g., dried *M. balsamina* plants. In one non-limiting embodiment, the method comprises the steps of: (a) forming an aqueous plant extract from a dried MOMO30-containing plant; (b) lysing plant cells therefrom so as to form an aqueous plant extract; (c) centrifuging the aqueous plant extract to remove debris and particulates and retaining the aqueous supernatant; (d) filtering the aqueous supernatant through a MW cutoff filter to sterilize and further purify the MOMO30 protein; and (e) eluting MOMO30 from the filter retentate into buffer for storage and/or use.

As further described below, MOMO30-containing extracts or purified proteins were tested for functional activity by testing their ability to inhibit infectivity by the MAGI cell infectivity assay (or "indicator assay") described above. In practice, the extracts are quite stable and have been stored freeze dried for years without significant loss of anti-viral activity.

MOMO30-containing plant extracts or purified proteins may be evaluated for functional activity by testing their ability to inhibit infection by HIV using a MAGI cell infectivity assay (or "indicator assay"). This assay involves the use of genetically modified CD4-expressing HeLa cell line (MAGI) containing an HIV LTR-driven cassette placed upstream of the *E. coli* β-gal encoded reporter gene (HeLa-CD4-LTR-β-gal) as described above. Cells infected by HIV turn blue and can be counted under a microscope. In the figures that follow, the results depict inhibition of infectivity as a function of blue cells per nanogram of HIV-1 p24 capsid protein. In some cases WT HIV-1 NL4-3 was used to allow multiple rounds of infectivity. By using HIV-1 NL4-3 with a deleted env gene and then supplying env in trans, the assay can test a single round of infectivity.

As shown in FIGS. 2A and 2B, both individual (C extract) and pooled (A-E extracts) *M. balsamina* plant extracts were found to inhibit HIV-1 infection of MAGI cells.

To determine if MOMO30-containing plant extracts inhibit HIV-1 replication in a "dose-dependent" manner, five different *M. balsamina* extracts (A-E) were tested individually or in combination (i.e., pooled) to evaluate their ability to inhibit HIV infection using the MAGI cell assay. As shown in FIG. 3A, infectivity of MAGI cells by HIV-1 was inhibited by each of the MOMO30-containing plant extracts (individually and in combination) in a dose-dependent manner. In FIG. 3B, the assay was conducted with an extract in which dried plant was field extracted in boiling water and then cooled in a pot using leaves. These results underscore the profound stability of MOMO30.

The extracts were further evaluated in a cellular viability (MTT) assay to see whether they are toxic to cells. The assay was conducted in HEK293 cells and the results showed that *M. balsamina* extracts containing MOMO30 were not toxic at concentrations needed to inhibit HIV infection over the concentrations tested (FIG. 4A). Subsequent analysis showed that the toxicity observed in Extract A could be separated on a sizing column from MOMO30 and was present in a lower molecular weight fraction than MOMO30 (data not shown).

To determine if the extract could block virus directly produced from infected cells (as opposed to purified virus), infected Jurkat T cells were mixed with uninfected cells at two different ratios 1:5 and 1:50 (infected:uninfected) in the absence (left half of panel) or presence (right half of panel) of Extract A. The results in FIG. 4B showed that the extracts did not significantly change the amount of virus progeny produced but had a large effect on the infectivity of the particles produced. This suggests that the extract inhibited re-infection by progeny virions produced from infected cells. Unexpectedly, it also suggests that exposure to the extract induced a change in the progeny virions produced, causing them to have lower intrinsic infectivity. This suggests that exposure to the extract increases the number of defective HIV particles that are produced.

To determine whether the antiviral properties of the active agent in the plant extracts are specific for HIV or could be extended to other viruses as a broad-spectrum antiviral agent, MAGI cell infectivity assays were extended to infections by simian immunodeficiency virus (SIV) and Ebola virus. The results of this analysis are shown in FIGS. 5A (SIV) and 5B (Ebola virus). These results are consistent with the active agent having broad-spectrum antiviral properties.

Physical and Chemical Properties of the Active Agent

To further characterize the chemical nature of the active product, various extraction conditions were applied to preparation of the evaluate extraction of the active product in the *Momordica balsamina* plant extracts. Accordingly, *M. balsamina* leaves were directly extracted in water, isopropyl alcohol (IPA), tetrahydrofuran (THF), acetylnitrile (ACN), ethanol (EtOH), and acetone (FIG. 6A). These extracts were evaluated for their ability to inhibit HIV infection of MAGI indicator cells, where lower bars indicate greater anti-viral activity). As shown in FIG. 6A, the active agent can be extracted using water and acetylnitrile. This suggests that the active agent has both hydrophilic and hydrophobic properties, which is characteristic of larger molecules, such as proteins. The water-soluble nature of the active agent was further confirmed when testing the aqueous and organic phases obtained following extraction of *M. balsamina* leaves with ethyl acetate, chloroform, hexane and diethyl ether (FIG. 6B).

To further characterize the size and physical properties of the active agent, the plant extracts were passed through filters having different molecular weight cut-offs (3, 20, 30 and 100 kDa). The resulting filtrates and retentates were then tested in MAGI cell indicator assays to correlate infectivity inhibition with the different fractions or treatments obtained as shown in FIG. 6A. Additionally, to evaluate the stability of the active agent to heat, the extract was heated above 60° C. for 20 min. and run through a 50 kDa cut-off filter. The results of this analysis are shown in FIG. 6B. Compared to the cut-off filters tested in FIG. 6A, a filter with a 50K MW cut-off size was found to provide the cleanest separation of active agent (FIG. 6B). Further, as shown in FIG. 6B, the heat treatment was found to have no effect on activity of the active agent. When subjecting the retentate (or residue) fraction obtained with the 30K filter to a Coomasie stained SDS PAGE 4-20% gradient gel, the active agent was identified as a protein of about 30 kDa in size that is sensitive to proteolysis by subtilisin (FIG. 6C). As shown in FIG. 6D, the size of the 30 kDa protein, referred to as MOMO30 herein, was further confirmed by SDS-PAGE analysis of an aqueous *M. balsamina* extract (middle lane, "Extract") and the retentate resulting from passage through a 30 kDa cutoff filter (right lane, "Purified"). The MOMO30 protein is responsible for >98% of the anti-viral activity of the water-soluble extracts discussed herein.

MOMO30 Binds to HIV-1 gp120

Figure 8A:
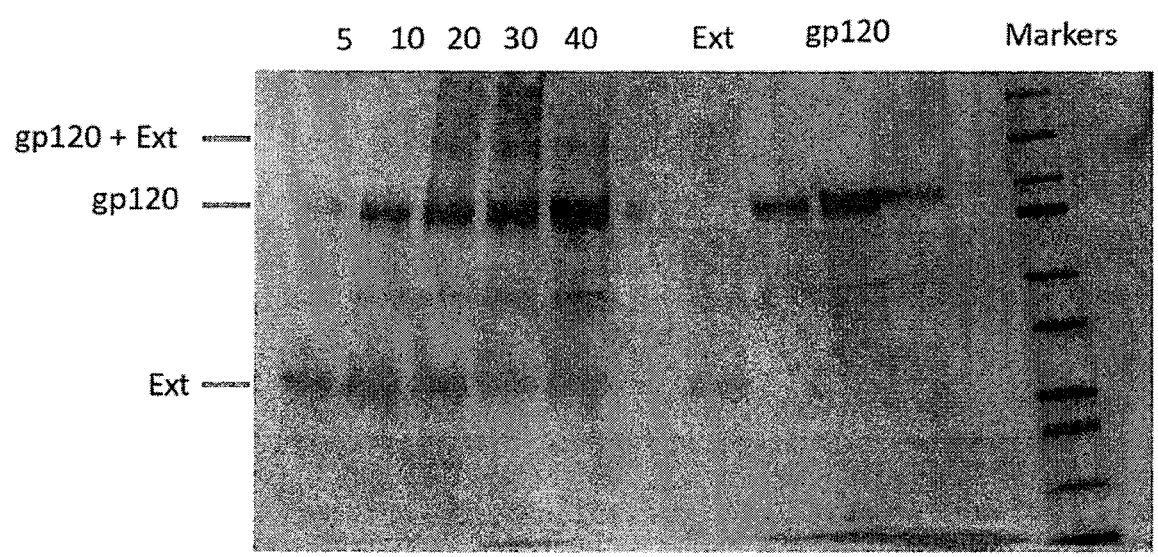
FIG. 8A is a Coomasie stained SDS-PAGE showing that the 30 kDa MOMO30 protein from extract A ("Ext") binds to increasing levels of purified HIV gp120 (in relative amounts 5, 10, 20, 30 and 40) and induces it to undergo a shift in MW (see "gp120+Ext"). Note the shift in mobility is evident even after boiling in loading buffer and despite the denaturing conditions in the gel.

To further characterize the antiviral properties of the 30 kDa protein, the aqueous plant extract was incubated with purified HIV-1 gp120 loaded on a non-denaturing polyacrylamide gel. The results of this analysis showed that the 30 kDa protein in the plant extract binds HIV-1 gp120 inducing a band-shift and that this interaction was not disrupted by boiling or denaturing conditions of the gel (FIG. 8A).

Figure 8B:
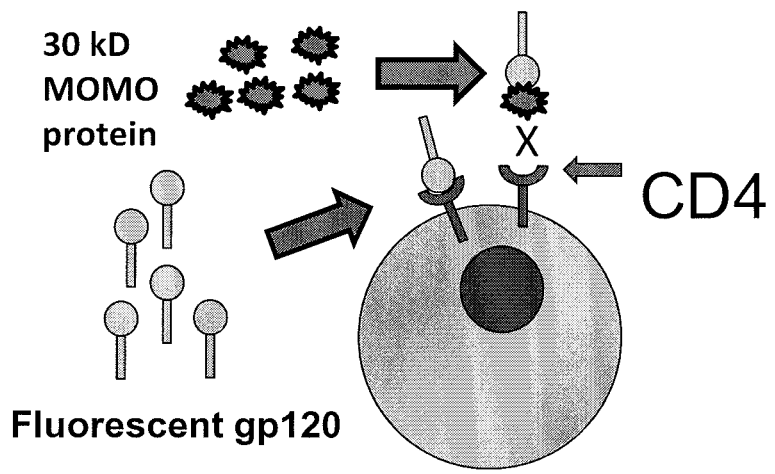
FIG. 8B is a schematic depiction of a blocking assay to examine whether MOMO30-containing extracts from *M. balsamina* inhibit the binding of purified HIV gp120 to CD4. Purified fluorescently labeled gp120 (30 µg, ImmunoDx) was added to $1 \times 10^6$ Jurkat T cells either with PBS or a pooled combination of extracts.
Figure 8C:
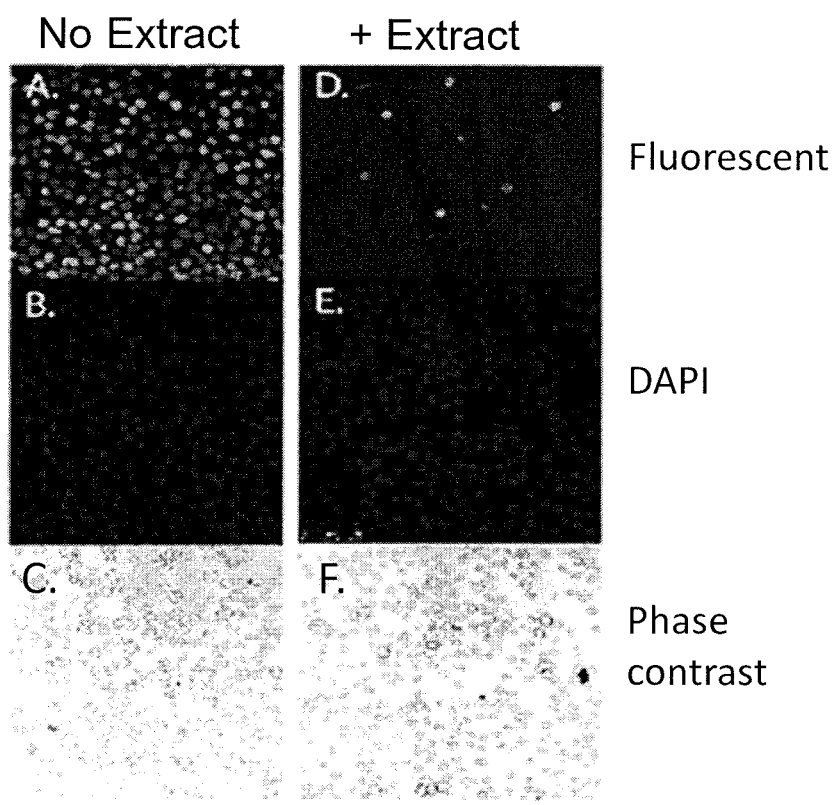
FIG. 8C shows the results of a fluorescence binding assay (as depicted in schematic in FIG. 8B). Briefly, Jurkat T cells are mixed with FITC labeled gp120 either in the absence (panels A-C) or presence (panels D-F) of extract A. The results show that binding of fluorescently labeled gp120 to the surface of Jurkat T-cells (panel A) was inhibited in the presence of the MOMO30-containing plant extracts (panel D). Panels B and E are the same cells stained with DAPI and panels C and F depict the same cells under phase contrast.

To further confirm this binding in the context of live cells, a blocking assay was carried out. FIG. 8B is a schematic depiction of the blocking assay which tested the ability of a MOMO30-containing extract to inhibit binding of purified HIV gp120 to its co-receptor CD4. In this assay, purified fluorescently labeled 30 μg of gp120 (ImmunoDx) was added in the presence or absence (PBS only) of a pooled combination of extracts to 1×106 Jurkat T cells. As shown in FIG. 8C, when incubated in the presence of 200 μg/ml of plant extract, almost complete inhibition of gp120 attachment to CD4 was obtained (compare panels A and D).

Figure 9:
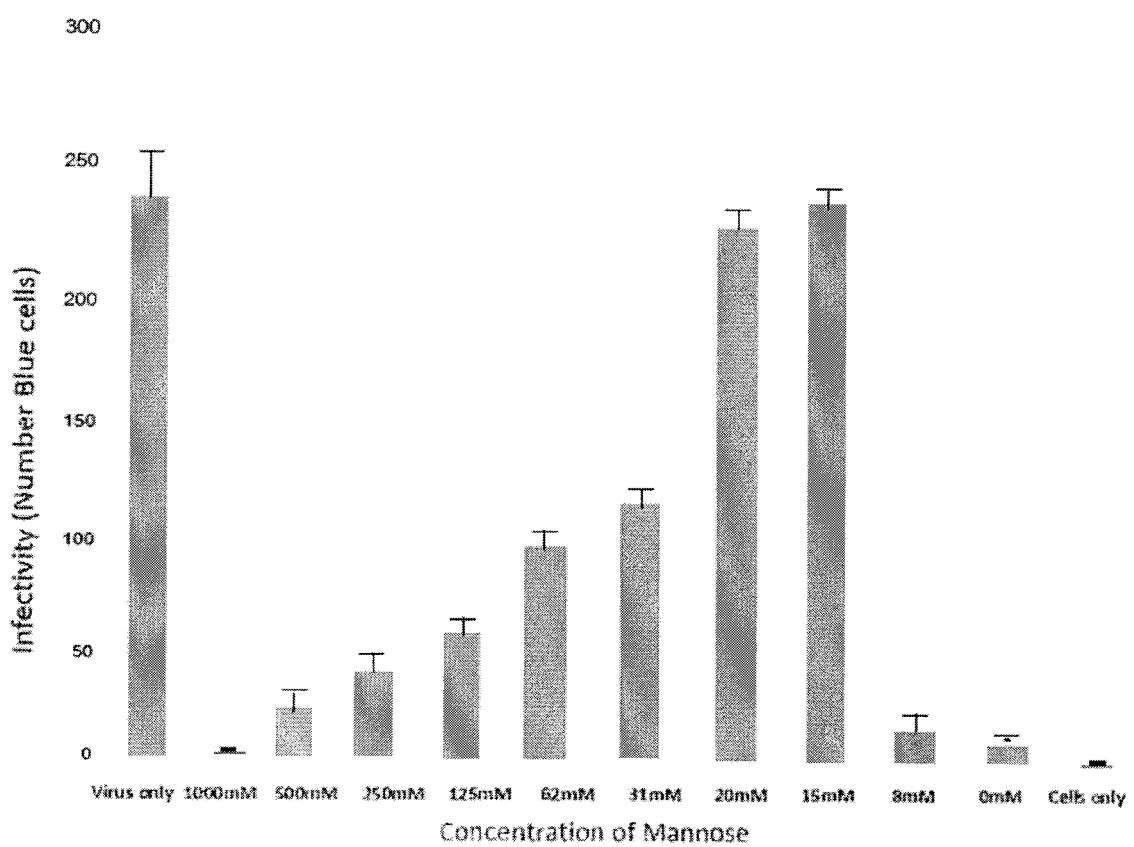
FIG. 9 depicts the results from MAGI cell indicator assays using MOMO30-containing plant extract A in the presence of increasing concentrations of the monosaccharide mannose where higher bars indicate "inactivation" of the inhibitory effect.

To further investigate the nature of the binding between the 30 kDa MOMO protein and gp120, MAGI indicator cells were infected with HIV in the presence of the plant extract at increasing concentrations of the monosaccharide mannose. HIV gp120 is known to undergo high-mannose glycosylation. The results of this analysis in FIG. 9 showed that while mannose concentrations of 15-20 mM virtually eliminated the ability of the MOMO30 protein in the extract to inhibit HIV infection, lower mannose concentrations had little effect on MOMO30's ability to inhibit HIV infection, and higher mannose concentrations had a progressively decreased ability to neutralize the inhibitory activity of MOMO30.

Figure 10A:
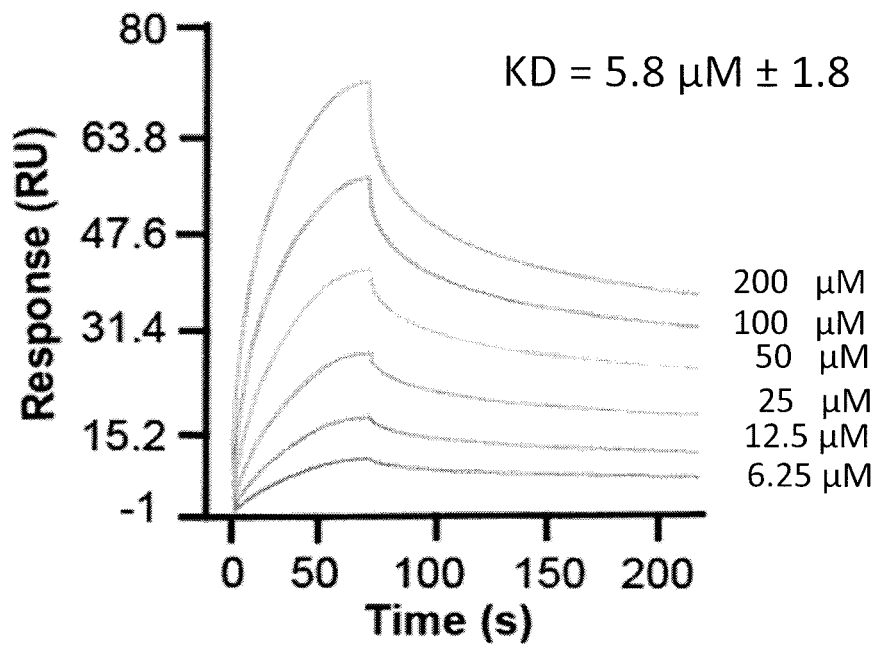
FIG. 10A shows a surface plasmon resonance (SPR) analysis (Biacore) indicating that MOMO30 protein from Extract A attaches to HIV gp120 so as to prevent its interaction with the CD4 receptor. Gp120 was immobilized on the gold surface and MOMO30 protein was flowed across the surface at concentrations from 6 to 200 nM. The assay was done in triplicate on separate days.
Figure 10B:
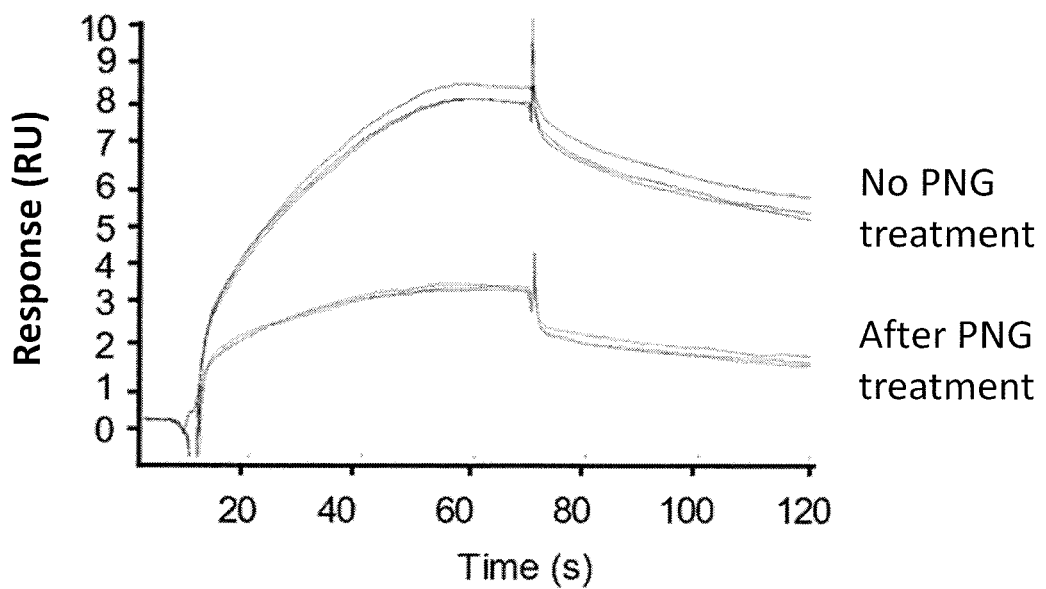
FIG. 10B shows that binding of MOMO30 to gp120 is dependent on glycosyl residues on gp120. A Biocore chip was saturated with gp120 and MOMO30 (top curves). The gp120-MOMO30 complexes were treated with PNG glycosylase to remove sugar residues from gp120 (bottom curves). Loss of sugar residues resulted in a decrease in binding.

To further examine the interaction between MOMO30 and purified gp120, surface plasmon resonance (Biacore) analysis was carried out. Gp120 was immobilized on the gold surface of a Biacore chip and increasing concentrations of MOMO30 protein (from 6.25 nM to 200 nM) were flowed across the surface and monitored by SPR. After 60 min, regeneration buffer as added to induce dissociation. The assay was done in triplicate on separate days. The results of this analysis are shown in FIG. 10A and indicate that MOMO30 bound to the surface in a concentration dependent manner with a KD of 5.8 μM±1.8. To further confirm that binding of MOMO30 to gp120 is dependent on glycosyl residues, such as mannose, on gp120, a Biacore chip was saturated with gp120 and MOMO30 to form gp120-MOMO30 complexes (FIG. 10B, top curves). The gp120-MOMO30 complexes were treated with PNGase F to remove sugar residues from gp120 (FIG. 10B, bottom curves). PNGase F is an amidase that works by cleaving between the innermost GlcNAc and asparagine residues of high mannose, hybrid, and complex oligosaccharides from N-linked glycoproteins and glycopeptides, resulting in a deaminated protein or peptide and a free glycan. In this case, the loss of sugar residues produced a decrease in reflectance units (RU), which reflects a decrease in MOMO30 binding to gp120.

Inhibition of Viral Infection

Figure 11:
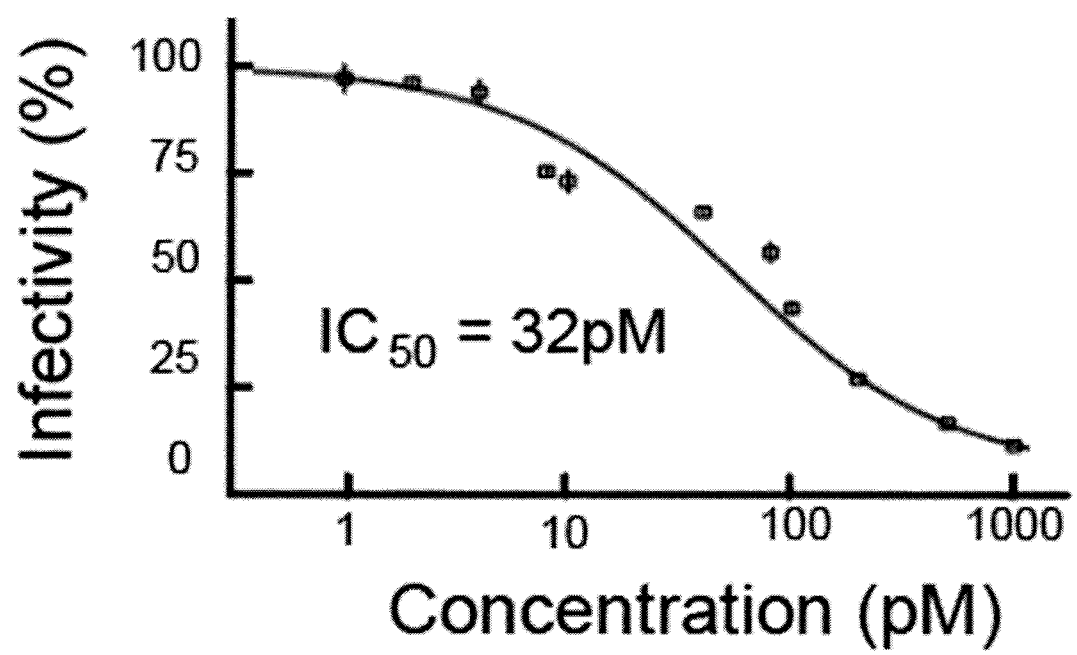
FIG. 11 depicts a MAGI infectivity assay for determining the IC50 of purified MOMO30 to block HIV-1 infection of the lab strain NL4-3. IC50 was determined by dose response at various MOMO30 protein concentrations.

FIG. 11 depicts a MAGI infectivity assay for determining the IC50 of purified MOMO30 to block HIV-1 infection of the lab strain NL4-3 as determined by dose response at various MOMO30 protein concentrations. The results of this assay showed the inhibition of HIV-1 infectivity by MOMO30 reflected in an IC50 of 32 pM, which is better than the IC50s of currently marketed HIV-1 fusion inhibitors, such as Maraviroc, Enfuvirtide and Ibalizumab.

Figure 5A:
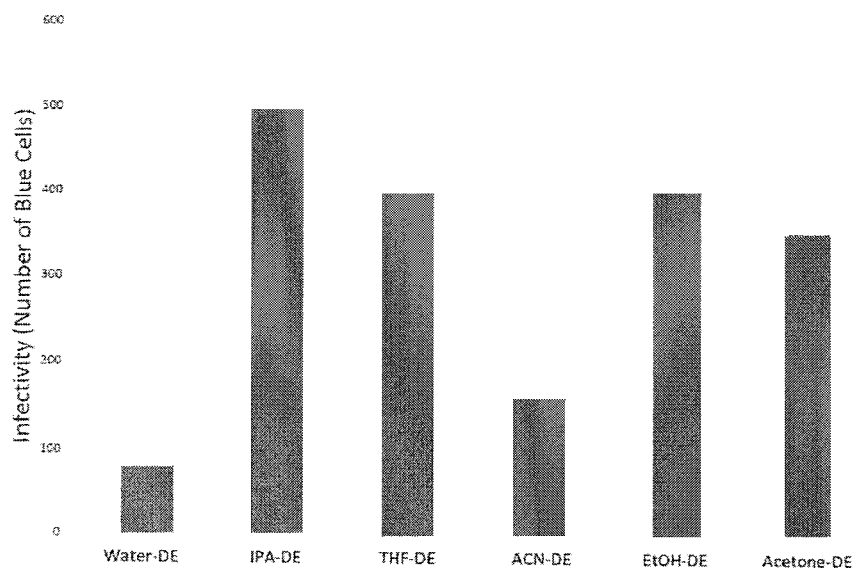
FIGS. 5A and 5B show the effects of different primary solvents (A) or extraction conditions (B) used in processing Extract A on the amount of inhibition of HIV as determined by MAGI cell indicator assays in which the lower bars indicate greater inhibition.
Figure 5B:
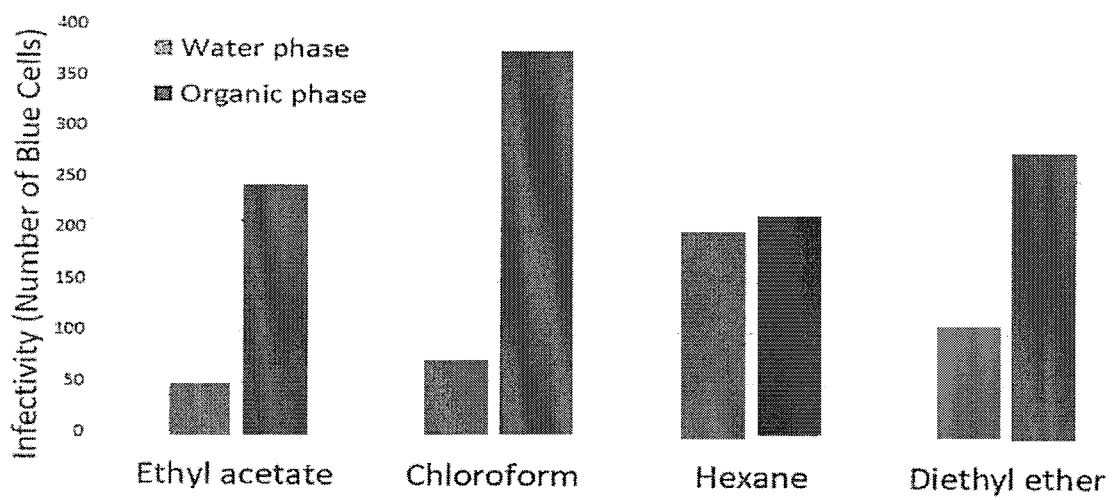
Figure 6A:
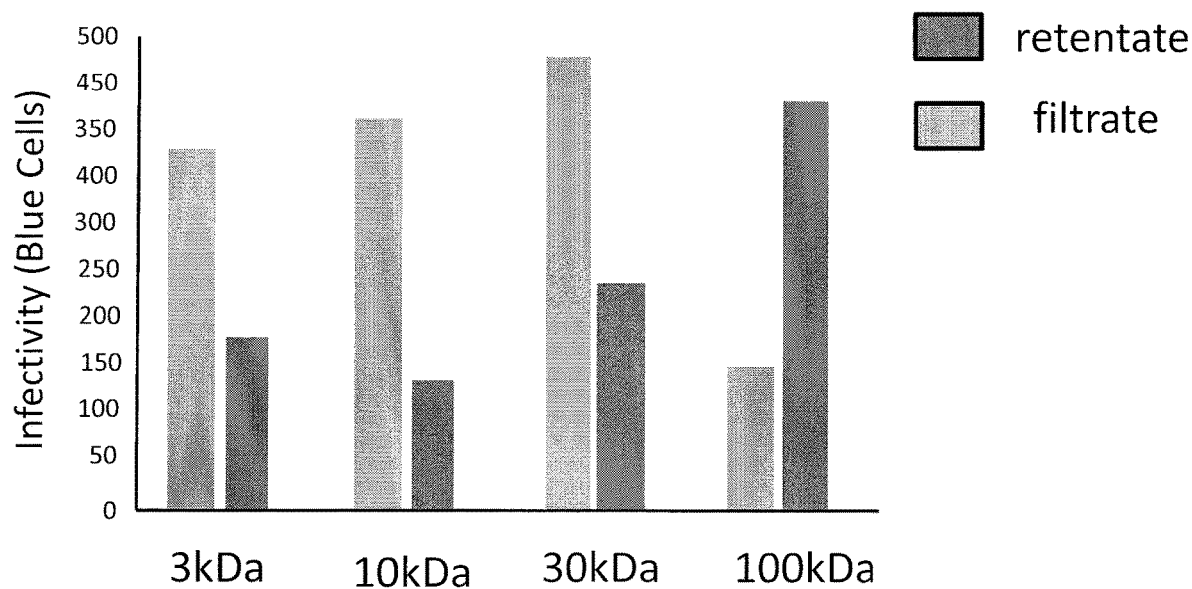
FIG. 6A shows the results from using different size molecular weight cutoff filters to either retain (retentate) or pass through (filtrate) the product in Extract A providing an inhibitory effect as determined by MAGI cell indicator assays in which the lower bars indicated greater inhibition. Note that most of the inhibitory effect was retained by a 30 k filter (Amicon).
Figure 6B:
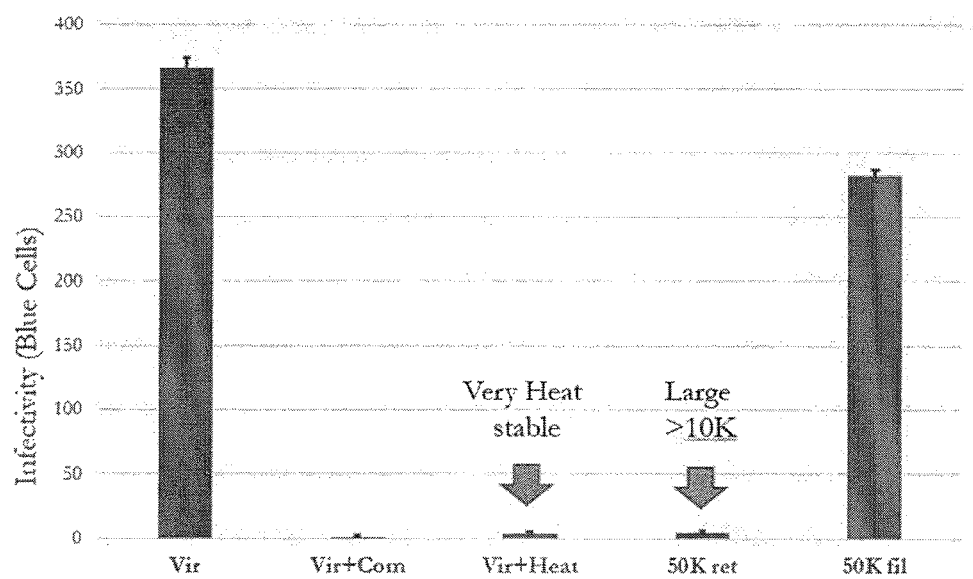
FIG. 6B shows repeat testing using an Amicon 50K cutoff filter. The retained material or retentate was also tested for heat stability by heating to 60° C. for 20 min which typically denatures most proteins. Vir+Com=virus plus compound (extract).
Figure 6C:
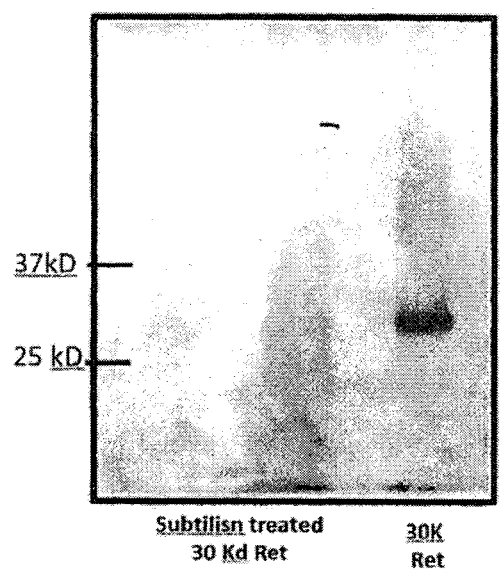
FIG. 6C shows a Coomasie stained SDS PAGE 4-20% gradient gel of the material retained by the cutoff filter showing that that the active agent is a 30 kDa protein (MOMO30) in size that is sensitive to proteolysis by subtilisin.
Figure 6D:
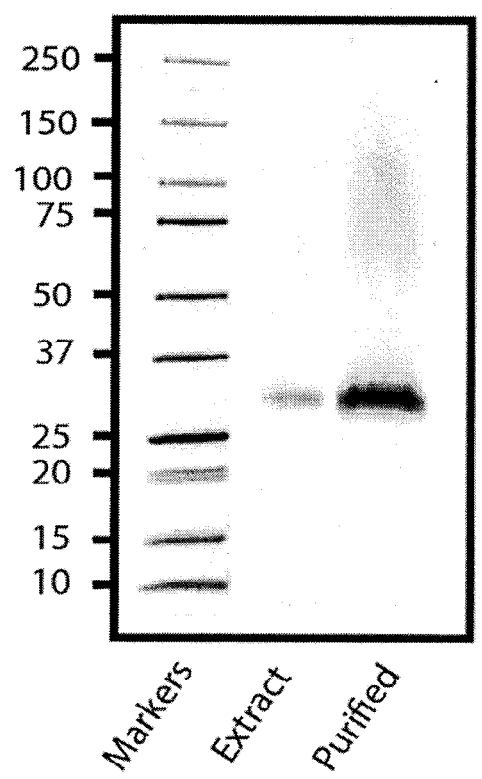
FIG. 6D shows an SDS-PAGE gel of the MOMO30 protein from unprocessed extract and the retentate of an extract passed through a 30K MW cut-off filter.
Figure 12:
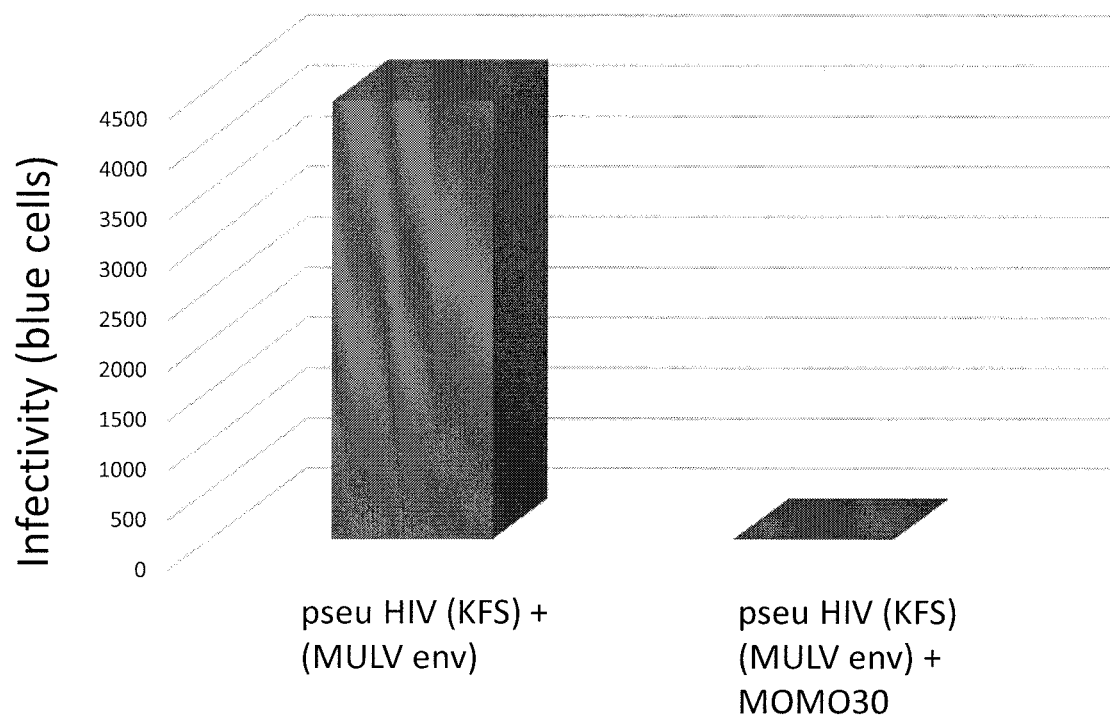
FIG. 12 shows that an HIV-1 pseudotyped with the aMLV envelope protein is sensitive to MOMO30 inhibition. An env deleted HIV-1 strain (KFS) pseudotyped to contain the MuMLV envelope glycoprotein was tested from infectivity in the absence (left) or presence (right) of MOMO30.

As noted above in FIGS. 5A and 5B, MOMO30-containing extracts were additionally found to inhibit simian immunodeficiency virus and Ebola virus. To further examine whether the antiviral activity of MOMO30 further extends to other enveloped viruses, an envelope (env) deleted HIV-1 strain (KFS) pseudotyped to contain the MuMLV envelope glycoprotein was tested for infectivity in the absence (left) or presence (right) of MOMO30 (FIG. 12). The results of this assay showed that an HIV-1 pseudotyped with the aMLV envelope protein is sensitive to MOMO30 inhibition, suggesting that the antiviral properties of MOMO30 broadly extend to a variety of enveloped viruses via glycosylated surface envelopes.

MOMO30 Causes Hemagglutination

Figure 13A:
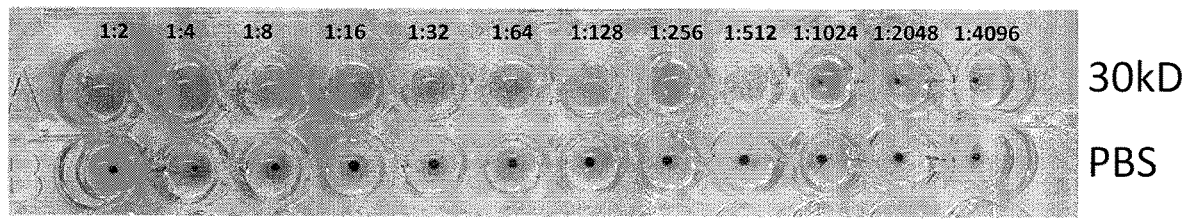
FIG. 13A shows that MOMO30 causes hemagglutination. Purified MOMO30 was tested for its ability to agglutinate sheep red blood cells (RBCs). As shown in panel A, the stock solution at a dilution of 1:512 was found to cause hemagglutination.

The observation that MOMO30 appears to bind sugar groups in a range of viral envelopes suggests that it has properties reminiscent of lectins. Inasmuch as lectins have often been found to exhibit hemagglutinin activity, it was of interest to investigate whether MOMO30 exhibits hemagglutinin activity too. FIG. 13A shows the results of this analysis. In this case, purified MOMO30 protein was tested for its ability to agglutinate sheep red blood cells (RBCs). As shown in panel A, a 30 mg/ml stock solution at a dilution of 1:512 was found to cause hemagglutination, consistent with lectin-like activity.

MOMO30 Stimulates the Activation and Proliferation of T Cells

Figure 13B:
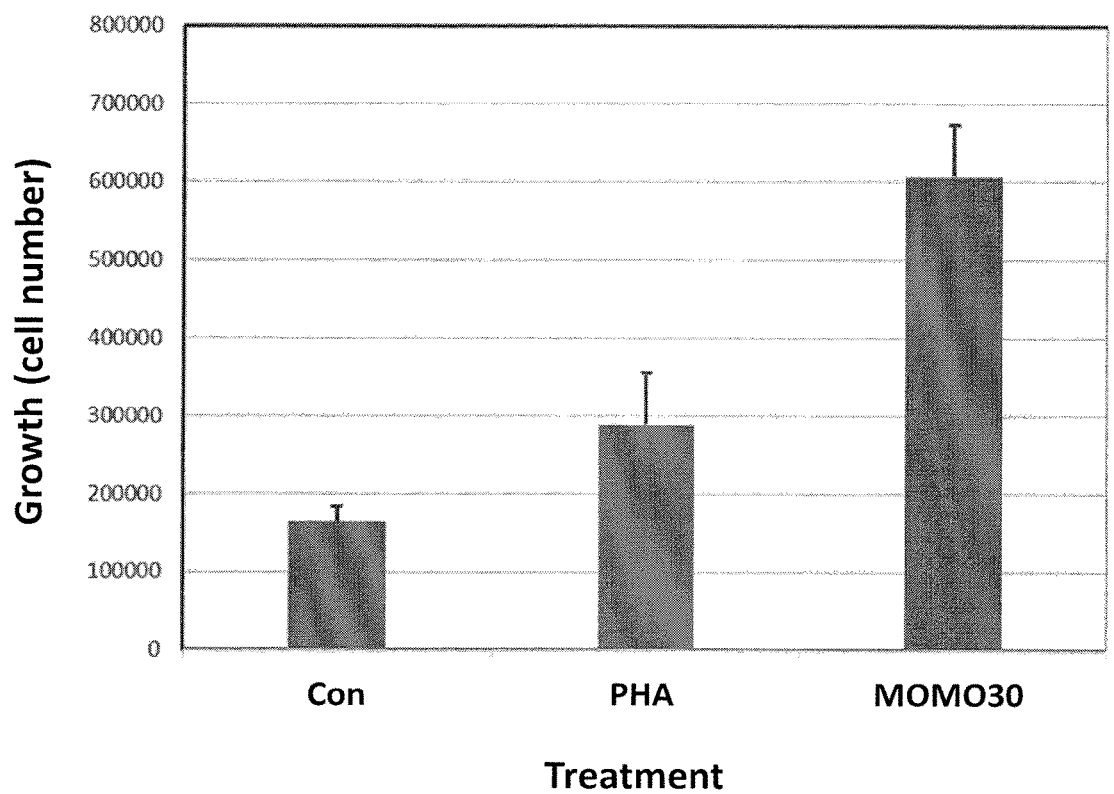
FIG. 13B shows that MOMO30 stimulates T cell growth. In each experiment, a fixed number of Jurkat cells was treated (left to right) with either PBS (control, Con), phytohemagglutinin A (PHA) or an equal amount of MOMO30.

Inasmuch as lectins are known to function as T cell mitogens, such as phytohemagglutinin A (PHA), it was of interest to examine whether MOMO30 can stimulate the activation and proliferation of T cells. Thus, a T cell activation assay was performed in which a fixed number of Jurkat cells was treated (left to right) with PBS (neg. control, Con), PHA (pos. control), or MOMO30 (FIG. 13B). The results of this assay showed that MOMO30 similarly stimulates the activation and proliferation of T cells.

Clinical Study of HIV Patients Treated With a MOMO30 Herbal Tea

Figure 14A:
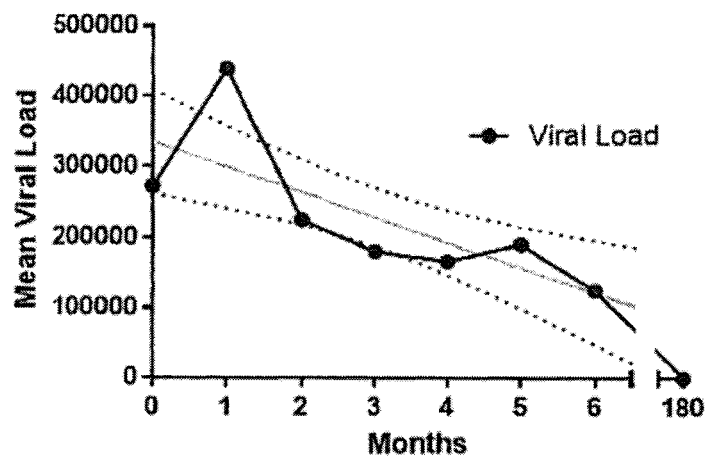
FIGS. 14A-14B show the results of a clinical study (n=61) in which HIV-1 infected patients were orally administered an herbal tea daily for 6 months containing Extracts A-E above. The results of this study showed a decrease in patients' HIV viral loads following a 6-month treatment with MOMO30 plant extract (FIG. 14A).
Figure 14B:
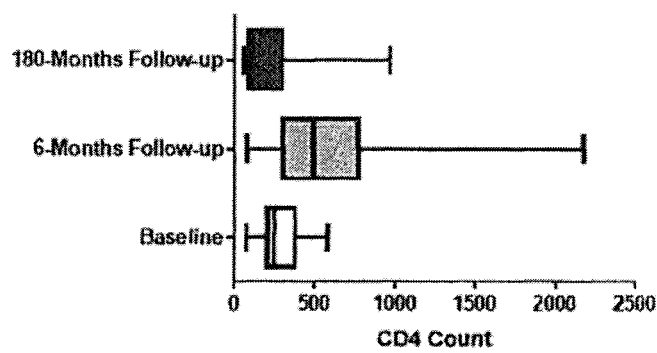

To examine the therapeutic efficacy of the 30 kDa MOMO30 protein, HIV-infected patients (n=61) were orally administered a combination of Extracts A-E daily for a period of 6 months during which no other anti-retroviral agents (ARVs) were administered. The extracts were administered in the form of an herbal tea. During this 6 month treatment period, the patients' viral loads (FIG. 14A) and CD4+ lymphocyte counts (FIG. 14B) were monitored. The results of this analysis showed that the average viral load was significantly reduced (FIG. 14A), while the CD4+ cell counts increased over this same period (FIG. 14B). A follow-up done over 10 years later (180 months) showed that some of the treated patients are healthy and exhibit undetectable or extremely low HIV virus levels (FIG. 14A).

In particular, Table 1 shows individual patient data evaluating viral loads and CD4+ cell counts in the follow-up patients compared to healthy, uninfected control subjects, where NP=Not performed (specimen clotted) and ND=Not detected<20 copies/ml.

TABLE 1

| Patient Number | % CD4+ cells/total lymphocytes | No. CD4+ cells/ml | No. total lymphocytes/ml | Viral Load (<20 copies) |
|---|---|---|---|---|
| Uninfected Control Subjects | | | | |
| 1 | 26 | 422 | 1630 | ND |
| 2 | 53 | 539 | 1019 | ND |
| 3 | 23 | 175 | 762 | ND |
| 4 | 50 | 116 | 230 | ND |
| 5 | 28 | 211 | 761 | ND |
| 6 | 21 | 374 | 1797 | ND |
| 7 | 32 | 139 | 434 | ND |
| 8 | 45 | 185 | 414 | ND |
| 9 | 28 | 82 | 298 | ND |
| 10 | 13 | 206 | 1634 | ND |
| 11 | 37 | 565 | 1518 | ND |
| 12 | 49 | 106 | 215 | ND |
| 13 | NP | NP | NP | ND |
| Control Avg | 34 | 260 | 893 | |
| Follow-Up Patients 10 Years After Treatment | | | | |
| 14 | 21 | 95 | 444 | ND |
| 15 | 36 | 61 | 170 | ND |
| 16 | 47 | 73 | 154 | ND |
| 17 | 16 | 146 | 895 | 3360 |
| 18 | 24 | 78 | 322 | ND |
| 19 | 33 | 969 | 2909 | 20 |
| 20 | 21 | 180 | 855 | ND |
| 21 | 32 | 95 | 294 | 3600 |
| 22 | 14 | 110 | 768 | ND |
| 23 | 29 | 314 | 1094 | ND |
| 24 | 32 | 283 | 892 | ND |
| 25 | 29 | 649 | 2253 | ND |
| 26 | 13 | 112 | 897 | ND |
| Patient Avg | 27 | 243 | 919 | |

The results of the follow-up study showed that the treated patients showed similar CD4 and viral load profiles compared to the uninfected control subjects.

Figure 15A:
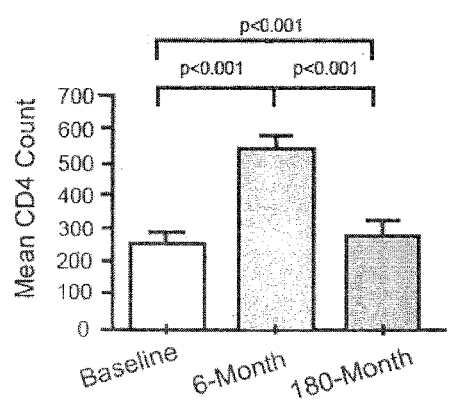
FIGS. 15A-15B further show the results of the clinical study in FIG. 14 where an increase in CD4+ lymphocytes of about 50% was observed following 6 months of treatment with the (FIG. 14A), and a decrease of 60% of the patients' mean HIV viral loads was observed following a 6-months post-treatment (FIG. 14B), which typically decreased to undetectable levels after 180 months (FIG. 14B).
Figure 15B:
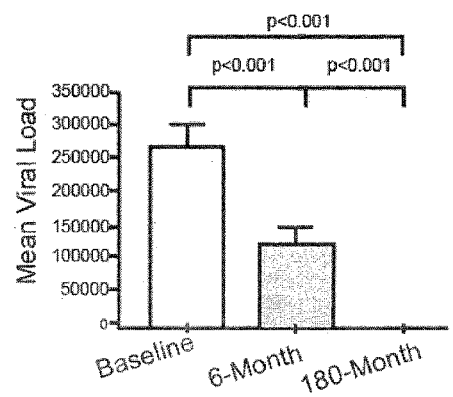
Figure 17:
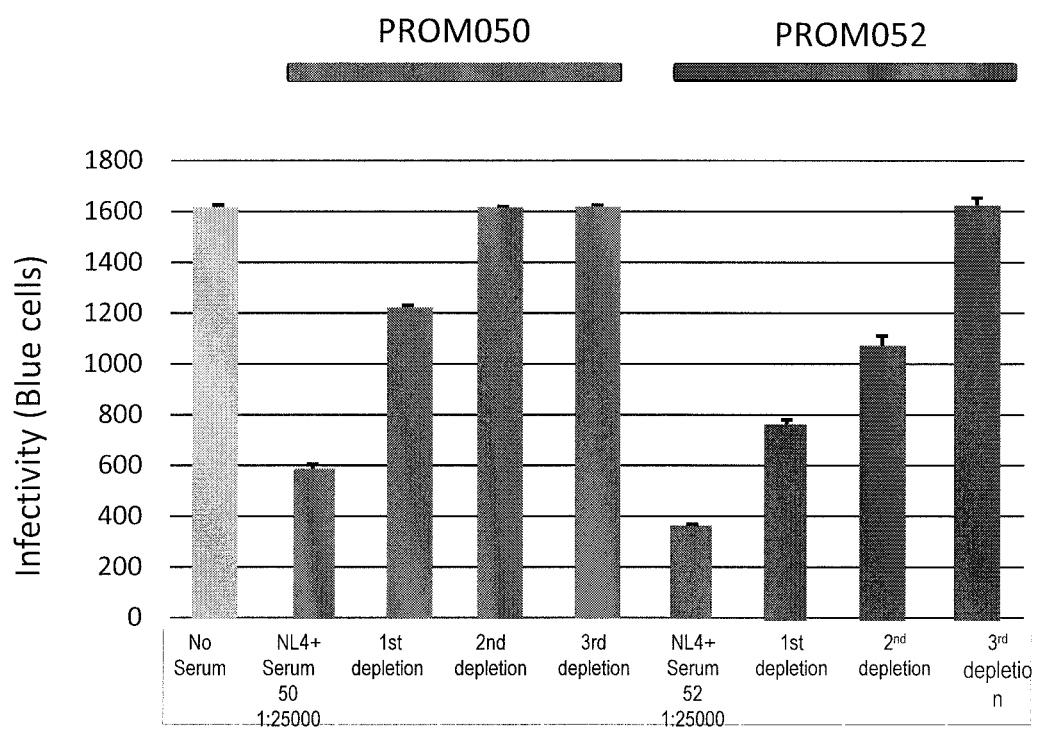
FIG. 17 shows the results of an analysis in which serum from two patients (PROM050 and PROM052) treated with Extracts A-E in FIGS. 1-4 above were tested for neutralizing activity against HIV NL4-3 following 3 successive rounds of Protein A/G adsorption. Following adsorption, neutralizing activity was completely depleted.

FIGS. 15A-15B further show the results of the clinical study above, further documenting an increase in CD4+ lymphocytes of about 50% following 6 months of treatment with MOMO30 plant extract (FIG. 15A), and a decrease of 60% of the patients' mean HIV viral loads following a 6-months post-treatment (FIG. 15B), and in most cases decreased to undetectable levels after 180 months (FIG. 15B).

In FIG. 15C, a subset of the original patients (n=13) were re-tested at 180 months. The results of this analysis showed that CD4 counts in most of the re-tested patients returned to near baseline levels. In addition, viral loads in most of these re-tested patients had decreased to undetectable (<20 copies/ml) levels at 180 months post-treatment.

Analysis of Neutralizing Antibody Production

Antisera from the subset of original patients (n=13) in FIG. 15C were further evaluated for production of neutralizing antibodies in an HIV neutralizing antibody assay as previously described (Simek et al., J. Virol., 83(14):7337-7348, July 2009). Multiple assay controls were set up to monitor each plate in a run and to allow for comparison of runs over time. The two types of controls included: (1) a control virus panel tested with all samples (sera, plasma, antibodies, etc.) and (2) an antibody control. The control virus panel includes the neutralization sensitive lab strain env, NL4-3; a less sensitive primary isolate env, JRCSF; and a specificity control env, amphotropic murine leukemia virus (aMLV) envelope. aMLV was used as a specificity control, because it is a non-HIV envelope and has not been found to be inhibitable by antibodies to HIV. Any inhibition of aMLV by plasma would be attributed to non-specific factors. The antibody control included a broadly neutralizing HIV+ plasma present on all control assay plates.

FIGS. 16A-16C summarize the results of the HIV neutralizing antibody assay using antisera obtained from the 13 re-tested patients at 180 months post-treatment. FIGS. 16A and B show the results of the patient PROM050 serum being tested in a MAGI indicator cell assay for neutralizing activity against HIV-1 pseudotyped with an NL4-3 env or an aMLV env, respectively. FIG. 16C shows a table depicting antibody titers from the 13 re-tested patients at 180 months post-treatment against each of an HIV-1 pseudotyped with an HIV-1 envelope from one or 10 primary strains or one of 3 lab strains of HIV-1, as indicated. In this case, the serum from each of these 13 patients was tested against 13 different isolates of HIV-1 in 5 different clades. The table in FIG. 16C summarizes reciprocal dilutions of the inhibitory dose to induce 50% reduction in replication of virus (ID 50) as measured in a MAGI indicator cell assay. Darker shaded areas depict higher titers, while the lighter shaded areas depict lower titers.

Seven of these individuals had high titers of antibody against all of the isolates. Six of the patients had lower levels of antibody. All of the patients had significant levels of neutralizing antibodies against the common lab strain NL4-3. Not wishing to be bound by theory, the results suggest that binding of MOMO30 to glycosyl groups of gp120 exerts pressure for selection of mutant viruses having fewer glycosyl groups so the virus will be less susceptible to MOMO30. Thus, viruses with fewer sugars will be more antigenic and allow the host to mount a neutralizing ab response.

The follow up patients were tested for neutralizing ab at 180 months. More than half of them show high levels of ab that can neutralize over a dozen strains of HIV-1. The pseudotyped strains were used to test different primary envelope proteins. MuMLV env was used as a negative control, since there was no expectation for subjects being infected with this mouse virus. However, half of the patients also had an antibody that could neutralize that control, suggesting a broadly cross-reactive antibody. These results suggest that neutralizing antibodies raised in response to MOMO30 are responsible for the long-term control of HIV infection.

FIG. 17 shows that the neutralizing activity of serum from two patients (PROM050 and PROM052) treated with MOMO30 is completely eliminated following 3 successive rounds of Protein A/G adsorption. Additionally, these results confirm that the inhibitory activity was solely attributed to antibodies rather than an effect caused by the use of other anti-retroviral agents.

Identification of MOMO30 Protein Sequence

N-terminal Edman degradation sequencing was carried out to determine the amino terminal sequence of the MOMO30 protein. FIG. 18A shows that MOMO30 protein comprises the predicted amino acid sequence of SEQ ID NO. 1. As shown in FIG. 18B, the amino-terminal sequence is virtually identical to the mature amino-terminal sequence corresponding to several different isolates of a hevamine-A-like protein from *Prosopis alba*. Hevamines are members of several families of plant chitinases and lysozymes that are important for plant defense against pathogenic bacteria and fungi and belong to the family 18 glycosyl hydrolases. Hevamines are known to hydrolyze linear polysaccharide chains of chitin and peptidoglycan. As described above, the MOMO30 protein is heat stable and resistant to most proteases, including trypsin, which is used in most liquid chromatography with tandem mass spectrometry strategies.

Production of Anti-MOMO30 Antibodies and Detection of MOMO30 Protein Based on the amino-terminal sequence of the MOMO30 protein, polyclonal antisera was generated in rabbits using a synthetic peptide containing the amino acid sequence in FIG. 18B sequence. As shown in FIG. 18C, Western blot analysis showed that the anti-MOMO30 antibody detects a 30 kDa protein from *M. balsamina* plant extracts, as expected. In addition, the anti-MOMO30 antibody was found to inhibit HIV-1 infection in a dose dependent manner using the MAGI cell indicator assay described above (FIG. 18D).

Figure 19:
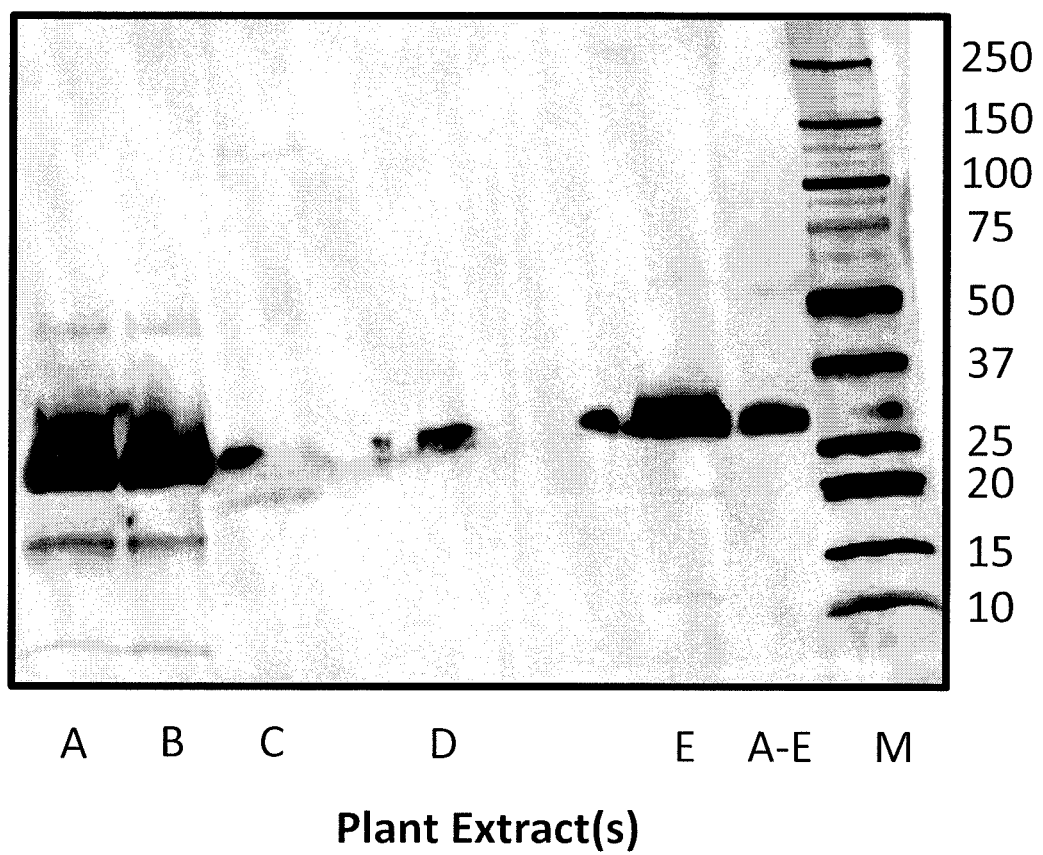
FIG. 19 shows the results of a western blot using the N-terminal polyclonal antibody from FIG. 18 for binding to the individual or pooled extracts evaluated in FIGS. 1-4 above.

FIG. 19 shows the results of a western blot using the rabbit polyclonal antibody from FIG. 18 for binding to the individual or pooled extracts evaluated in FIGS. 1-4 above (i.e., Extracts A-E). The results of this analysis suggest that the antibody is cross-reactive for a 30 kDa MOMO30 or MOMO30-related protein from different and distinct plants, including *M. balsamina*.

Evaluation of Chitinase Activity

Figure 20:
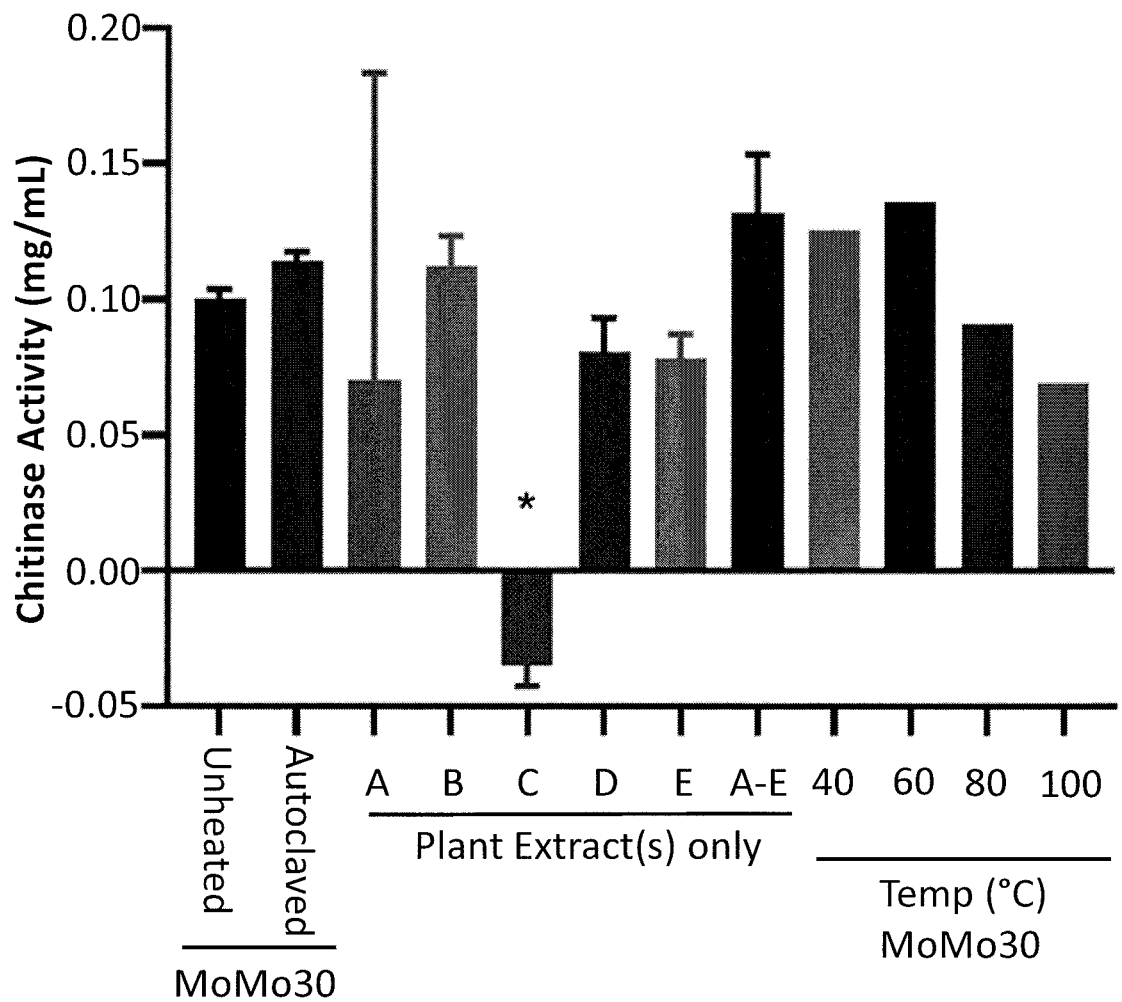
FIG. 20 shows the results of a chitinase assay using the individual or pooled extracts evaluated in FIGS. 1-4 above. The assay is initiated via enzymatic hydrolysis of chitin by chitinase(s) present in the extract(s). The enzyme catalyzed reaction product, N-acetylglucosamine reacts with PDAB, which is measured at a colorimetric readout at 585 nm.

In view of the N-terminal amino acid sequence consistent with properties shared by hevamines having chitinase properties, it was of interest to see whether the MOMO30 protein similarly exhibits chitinase activity. Thus, the Chitinase Microplate Assay Kit (MyBioSource, Inc., San Diego, Calif.) was employed according to the manufacturer's instructions. FIG. 20 shows the results of this analysis using the individual or pooled extracts evaluated in FIGS. 1-4 above (i.e., Extracts A-E). The assay is initiated via enzymatic hydrolysis of chitin by chitinase(s) present in the extract(s). The enzyme catalyzed reaction product, N-acetylglucosamine reacts with PDAB, which is measured at a colorimetric readout at 585 nm. The results suggest that the extracts contain a 30 kDa MOMO30-related protein having chitinase activity.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for preventing or reducing symptoms of HIV infection, comprising orally administering to a subject in need thereof an effective amount of a MOMO30 protein composition prepared by a method comprising the steps of:
   (a) drying a plant comprising MOMO30 protein;
   (b) lysing cells from the plant in an aqueous medium to form a plant cell lysate;
   (c) centrifuging the plant cell lysate to remove debris and particulates to form a clarified plant cell lysate; and
   (d) preparing a MOMO30 protein composition from the clarified plant cell lysate so that the MOMO30 protein composition is substantially free of plant components less than 10 kDa in size, and
   (e1) passing the clarified plant cell lysate through a molecular weight cut-off filter and collecting the MOMO30-containing retentate; and
   (e2) purifying the MOMO30 protein from the clarified plant cell lysate by immunoaffinity purification using an anti-MOMO30 antibody,
   wherein the MOMO30 protein composition comprises a MOMO30 protein that is about 30 kDa in size, stable after boiling at 100° C. for 20 min, binds HIV gp120, and comprises the amino acid sequence of SEQ ID NO: 1, and
   wherein the MOMO30 protein composition is orally administered to the subject in liquid or dried form.

2. The method of claim 1, wherein the MOMO30 retentate is eluted in an aqueous buffer to form an aqueous MOMO30 protein composition in solution.

3. The method of claim 2, wherein the MOMO30 protein composition is dried and administered in a dried form.

4. The method of claim 3, wherein the dried form is a capsule or tablet.

5. The method of claim 3, wherein the dried form is administered as an herbal tea to the subject.

6. The method of claim 2, wherein the MOMO30 solution is added to one or more pharmaceutically acceptable carriers and orally administered to the subject as a liquid.

* * * * *

```
                         SEQUENCE LISTING

<160> NUMBER OF SEQ ID NOS: 1

<210> SEQ ID NO 1
<211> LENGTH: 16
<212> TYPE: PRT
<213> ORGANISM: Momordica balsamina
<220> FEATURE:
<223> OTHER INFORMATION: synthesized
<220> FEATURE:
<221> NAME/KEY: misc_feature
<222> LOCATION: (12)..(12)
<223> OTHER INFORMATION: Xaa can be any naturally occurring amino acid

<400> SEQUENCE: 1

Gly Pro Ile Val Thr Tyr Trp Gly Gln Asn Val Xaa Glu Gly Glu Leu
1               5                   10                  15
```